United States Patent
Ito

(10) Patent No.: US 8,578,758 B2
(45) Date of Patent: Nov. 12, 2013

(54) GAS SENSOR AND METHOD FOR PRODUCTION THEREOF

(75) Inventor: Daisuke Ito, Kanagawa (JP)

(73) Assignee: Sony Corporation, Tokyo (JP)

( * ) Notice: Subject to any disclaimer, the term of this patent is extended or adjusted under 35 U.S.C. 154(b) by 1018 days.

(21) Appl. No.: 11/621,876

(22) Filed: Jan. 10, 2007

(65) Prior Publication Data

US 2007/0199819 A1    Aug. 30, 2007

(30) Foreign Application Priority Data

Jan. 11, 2006 (JP) .................................. 2006-003905

(51) Int. Cl.
G01N 27/12 (2006.01)

(52) U.S. Cl.
USPC ............ 73/31.06; 73/31.05; 73/23.2; 422/83; 422/88; 422/98; 204/424

(58) Field of Classification Search
USPC .......................................... 422/88; 204/424
See application file for complete search history.

(56) References Cited

FOREIGN PATENT DOCUMENTS

| JP | 07-198651 | 8/1995 |
|---|---|---|
| JP | 08-094560 | 4/1996 |
| JP | 2002-323467 | 11/2002 |
| JP | 2003-279517 | 10/2003 |
| JP | 2004-093388 | 3/2004 |
| JP | 2004-205294 | 7/2004 |
| JP | 2005-098947 | 4/2005 |
| JP | 2005-134311 | 5/2005 |
| JP | 2005-144569 | 6/2005 |
| JP | 2005-321326 | 11/2005 |
| JP | 2006-003153 | 1/2006 |
| WO | 2004-048957 A1 | 11/2002 |

OTHER PUBLICATIONS

Seal et al., Nanocrystalline SnO gas sensors in view of surface reactions and modifications, 2002, Springer, JOM vol. 54 No. 9, p. 35-38.*
Barsan et al., Conduction model of metal oxide gas sensors, 2002, Kluwer Academic Publishers, Journal of Electroceramics 7, p. 143-167.*
Kolmakov et al., Enhanced gas sensing by individual SnO2 nanowires and nanobelts functionlized with Pd catalyst particles, 2005, ACS, Nano Letters vol. 5 No. 4, p. 667-673.*
Hu et al., A new form of nanosized SrTiO3 material for near-human-body temperature oxygen sensing applications, Jun. 19, 2004, ACS, J. Phys. Chem. B 2004, 108, 11214-11218.*
Srivastava et al., Development of high sensitivity tin oxide based sensors for gas/odour detection at room temperature, Sensots and Actuators B 50 (1998) 175-180.*
Minoura et al., "Production of the titanium oxide surface having nano-honeycomb structure", Jun. 1, 2000, pp. 33-41, vol. 38.
Japanese Office Action for corresponding JP2006-003905 issued on Mar. 1, 2011.

* cited by examiner

*Primary Examiner* — In Suk Bullock
*Assistant Examiner* — Robert Eom
(74) *Attorney, Agent, or Firm* — K&L Gates LLP

(57) ABSTRACT

A gas sensor is provided. The gas sensor includes a gas-sensitive layer which changes in its characteristic properties upon contact with a detectable gas. The gas-sensitive layer has as the main sensitive part, a polycrystalline layer composed of a large number of uniform nano-size microcrystal grains which join together in the planar direction.

14 Claims, 20 Drawing Sheets

(STEPS a AND b)

(STEPS c AND d)

(STEP e)

(STEP f)

(STEP g)

(STEP h)

RAPID HEATING (STEPS i AND j)

(STEP k)

(STEP l)

(STEPS m AND n)

(STEP o)

(STEP p)

GAS SENSOR AND METHOD FOR PRODUCTION THEREOF

CROSS REFERENCES TO RELATED APPLICATIONS

The present application claims priority to Japanese Patent Application JP 2006-003905, filed in the Japanese Patent Office on Jan. 11, 2006, the entire contents of which is being incorporated herein by reference.

BACKGROUND

The present disclosure relates to a gas sensor and, more particularly, to a highly sensitive gas sensor with a gas-sensitive layer of metal oxide that works at normal temperature.

Among known gas sensors are those which have a gas-sensitive layer which changes in its physical properties upon contact with a detectable gas, thereby achieving gas detection. The one having a gas sensitive layer of metal oxide semiconductor finds general use as gas leak alarms.

Any gas sensor with tin oxide ($SnO_2$) to detect a reducing gas, such as combustible gas, works on the principle illustrated in FIGS. 20A and 20B. The gas sensor 100 consists of the alumina substrate 101, the counter electrodes 103 formed thereon, and the gas sensitive layer 102 of tin oxide semiconductor which covers the counter electrodes and fills the space between the counter electrodes. The gas-sensitive layer 102 is connected in series to the current detecting resistance 104 and the circuit power source 105 through the counter electrodes 103. The current detecting resistance 104 generates the output voltage 107 across its terminals to indicate the circuit current 106 flowing through the gas sensitive layer 102.

The gas-sensitive layer 102 adsorbs the oxygen molecules 109 on its surface because the tin oxide ($SnO_2$) as its constituent is an n-type semiconductor compatible with oxygen in air. The adsorbed oxygen molecules 109 constrain the conduction electrons 108b near the surface, thereby forming the surface depletion layer 102b near the surface. This results in a hindrance to the conduction of electrons in the gas-sensitive layer 102. Incidentally, FIGS. 20A and 20B have been drawn for brevity on the assumption that the gas-sensitive layer 102 is a mono-crystal layer and its top surface is in contact with air.

When exposed to clean air, the gas-sensitive layer 102 adsorbs at a maximum the oxygen molecules 109 on its surface, as shown in FIG. 20A. As the result, the surface depletion layer 102b reaches its maximum thickness, with the gas-sensitive layer 102 increasing in resistance and the circuit current 106 decreasing.

By contrast, when exposed to air containing a reducing gas (such as alcohol and hydrogen), the gas-sensitive layer 102 has the adsorbed oxygen molecules 109 thereon partly removed by reaction with the reducing gas molecules 111, as shown in FIG. 20B. The removed oxygen molecules 110 release the bound conduction electrons 108b, allowing them to function as the conduction electrons 108a. As the result, the surface depletion layer 102b decreases in thickness and the gas-sensitive layer 102 decreases in resistance, thereby causing the circuit current 106 to increase. Thus, the increase in electron conduction (or the decrease in resistance) indicates the concentration of the reducing gas molecules 111.

For enhancement of detection sensitivity and gas selectivity, the gas sensor 100 is usually incorporated with a noble metal catalyst (not shown) in or on the gas-sensitive layer 102. This catalyst promotes the surface reaction between the adsorbed oxygen 109 and the reducing gas 111. The gas sensor 100 with a low sensitivity at normal temperature is also provided with the heater 116 to heat it to about 300° C. to promote the surface reaction.

The gas-sensitive layer 102 greatly changes in conductivity depending on the concentration of the reducing gas molecules 111 as mentioned above. However, this change takes place only in the region where the surface depletion layer 102b forms. Thus, conductivity changes only slightly in the inner bulk layer 102a. For the change in concentration of the reducing gas molecules to be detected in terms of large change in the output voltage 107, it is important that the gas-sensitive layer 102 should have the bulk layer 102a in as small of a ratio as possible or should be as thin as possible.

Although it is assumed for brevity that the gas-sensitive layer 102 shown in FIGS. 20A and 20B is a mono-crystal layer, the ordinary gas-sensitive layer 113 schematically shown in FIG. 21 is a polycrystal layer composed of a large number of microcrystals 112 joined together. In this case, the following two points should be taken into account.

The first point is that the adjoining two microcrystals 112 in the polycrystal layer are in contact with each other, with the grain boundary 112c interposed between them, and hence the conduction electrons 108a flowing in the gas-sensitive layer 113 move through the grain boundary 112c. Contact at the grain boundary 112c between the two microcrystals 112 is usually made through the surface depletion layer 112b. Consequently, the conduction electrons 108a vary in the boundary potential they receive at the grain boundary 112c in response to the change in concentration of the detectable gas 114. This leads to the change in dynamic state of the conduction electrons 108a passing through the grain boundary 112c. In other words, the polycrystalline gas-sensitive layer 113 performs its gas sensing function by means of the grain boundary potential which plays an essential part. Therefore, any high sensitive gas sensor should be constructed such that the grain boundary 112c greatly changes in conductivity in response to the change in concentration of the detectable gas 114.

The second point is that the gas-sensitive layer 113 of laminate structure as shown in FIG. 21, in which the microcrystal grains 112 form multiple layers instead of a monolayer, requires the detectable gas 114 to diffuse to its lower layer so that it performs its function.

Attempts are being made to reduce as much as possible the particle size of the microcrystal grains of semiconductor (such as tin oxide), thereby reducing the ratio of the bulk layer 102a in a thick film sensor or thin film sensor to increase its sensitivity. However, the attempts have been unsuccessful so far because the microcrystal grains with a reduced particle size in laminate structure as shown in FIG. 21 have intergrain gaps that are too small to permit the detectable gas 114 to reach the lower layer by diffusion. Moreover, the gas sensor of laminate structure has a low response speed because it prevents the detectable gas 114 from rapidly entering and leaving the gas-sensitive layer 113 by diffusion.

There has been proposed a gas sensor in Japanese Patent Publication No. Sho 62-28420 (p. 2, FIG. 2) from the forgoing point of view. This gas sensor has a gas-sensitive layer of an oxide of perovskite structure, which is formed by plasma spraying and subsequent cooling to make a large number of fine cracks. The gas-sensitive layer with fine cracks allows for easy diffusion of the detectable gas.

There has also been proposed a gas-sensitive layer of different type than mentioned above. It is not a solid in simple shape with a size of the order of micrometers but is in the form of fine filament or tube with a diameter of the order of nanometers or thin film with a thickness of the order of nanometers, so that it has a large surface area to volume ratio.

An example of such a gas-sensitive layer is disclosed in Japanese Patent Laid-open No. 2005-144569 (pp. 3 to 5, FIGS. 1 to 5 and 9). It consists of a lower layer of two-dimensionally arranged fine particles of silicon oxide ($SiO_2$) and an upper layer of tin oxide ($SnO_2$).

The gas-sensitive layer disclosed in Japanese Patent Laid-open No. 2005-144569 is shown in FIG. 22 (partly enlarged top view and sectional view). As shown in FIG. 22, the gas sensor 120 consists of the flat substrate 121, the silicon oxide fine particles 122 which are two-dimensionally arranged in large number, and the gas-sensitive layer 124 of tin oxide ($SnO_2$) formed by vacuum deposition (which covers the layer of silicon oxide fine particles).

The layer of silicon oxide fine particles is formed by densely arranging the fine particles (with a diameter of about 100 nm) such that they come into contact with one another and then performing dry etching on them so that they decrease in diameter and the fine particles 122 are separated by the gaps 123 (several nanometers to tens of nanometers). The gas-sensitive layer 124 is formed on the fine particles 122, so that the fine particles 122 are covered individually by the semispherical coatings 125. The semispherical coatings 125 are joined by the bridge 126 at the gap 123 between the fine particles. The coatings 125 function in the same way as the fine crystal particles 112 of tin oxide shown in FIG. 21 and the bridge 126 functions in the same way as the grain boundary 112c shown in FIG. 21.

Japanese Patent Laid-open No. 2005-144569 mentions that the foregoing structure improves the sensitivity of the gas sensor because the gas-sensitive layer 124 is formed such that the coatings 125 in large number are joined together by the extremely fine bridges 126 and the shape of the bridge 126 is controlled by the size of the gap 123.

There is also disclosed a gas sensor of another type in Japanese Patent Laid-open No. 2002-323467 (pp. 3, 5, and 6, FIG. 3), in which the gas-sensitive layer is a polycrystalline mono-layer composed of two-dimensionally arranged microcrystal grains of metal oxide semiconductor.

The gas-sensitive layer (and the vicinity thereof) disclosed in Japanese Patent Laid-open No. 2002-323467 is shown in section in FIG. 23. According to the disclosure, the gas-sensitive layer 133, which is formed on the flat substrate 131, is a polycrystalline mono-layer of two-dimensionally arranged microcrystal particles 132 of metal oxide such as tin oxide ($SnO_2$). The microcrystal particles 132 should have as large an average particle diameter as possible in the plane direction (which is at least larger than the average particle diameter in the thickness direction). Also, the gas-sensitive layer 133 should have a thickness of 3 nm to 12 nm, which is smaller than the thickness of the surface depletion layer which occurs when the gas-sensitive layer 133 adsorbs the detectable gas.

The gas-sensitive layer 133 is formed in the following manner. First, the substrate 131 is finished flat by mechanical polishing and then cleaned by acid or alkali washing, so that its surface irregularities are smaller than one-fifth the thickness of the gas-sensitive layer 133.

Then, the substrate 131 is coated with the gas-sensitive layer 133 by the atomic layer growing method, which consists of alternately repeated steps of supplying the substrate surface with a gas containing metal elements constituting the gas-sensitive layer 133 and supplying the substrate surface with water, every consecutive two steps forming one atomic layer on the substrate 131.

The gas-sensitive layer 133 formed on the smooth surface of the substrate 131 as mentioned above have a uniform composition and hence consists of coarse microcrystals. This is because the smooth surface and the uniform composition help form coarse microcrystals.

The thus obtained gas-sensitive layer 133 is a polycrystalline mono-layer in which there is only one particle in the thickness direction and there are limited grain boundaries 132c between the microcrystal grains 132. Japanese Patent Laid-open No. 2002-323467 mentions that the polycrystalline mono-layer and the limited grain boundaries 133 minimize the diffusion of the detectable gas into the gas-sensitive layer 133, thereby contributing to a rapidly responsive gas sensor.

The gas-sensitive layer disclosed in Japanese Patent Publication No. Sho 62/28420 is an extremely thin solid of simple shape (of the order of micrometers) having a low ratio of surface area. It makes it difficult for the detectable gas to diffuse deep into it even though it has gas diffusion paths formed therein by cracking or the like because such gas diffusion paths are very long. In addition, it lacks uniform sensing characteristics because it involves more difficulties in evenly distributing the metal catalyst within the oxide fine particles or on the particle surface as the particle size decreases.

Also, the gas-sensitive layer 124 shown in Japanese Patent Laid-open No. 2005-144569 has a high ratio of surface area but is so brittle that the silicon oxide fine particles 122 are liable to peel off from the substrate 121. Moreover, it needs a complex crosslinking process for the bridges 126 to be formed uniformly at all times regardless of the gap 123 varying in size. In addition, the fact that the gas-sensitive layer 124 does not have a flat surface is unfavorable for the metal catalyst to be distributed to desired positions.

The gas-sensitive layer 133 disclosed in Japanese patent Laid-open No. 2002-323467 is based on the idea of reducing the grain boundaries 132c as far as possible. This idea seems contradictory to the sufficient sensitivity because the grain boundaries 132c become less sensitive as they decrease. In addition, the gas-sensitive layer 133 should have an accurately controlled thickness if the resulting gas sensors are to have uniform characteristics. This objective will be achieved only at the sacrifice of many processes including highly accurate processes, low productivity and yields, and high production cost.

Finally, the gas sensors disclosed in Japanese Patent Publication No. Sho 62/28420, Japanese Patent Laid-open No. 2005-144569 and Japanese patent Laid-open No. 2002-323467 are poor in sensitivity and stability at normal temperature and hence needs heating to a high temperature. This consumes electric power and endangers their use under certain circumstances.

The present invention was completed to address the above-mentioned problems. It is desirable to provide a gas sensor and a method for production thereof, the gas sensor being highly sensitive, small in size, and capable of stable operation with low power consumption at normal temperature, and the method allowing for efficient, uniform production at low cost.

SUMMARY

The first embodiment of the present invention is directed to a gas sensor having a gas-sensitive layer which changes in its characteristic properties upon contact with a detectable gas, wherein the gas-sensitive layer has as the main sensitive part a polycrystalline layer composed of a large number of uniform nano-size microcrystal grains which join together in the planar direction.

The second embodiment is directed to a method for production of a gas sensor having a gas-sensitive layer which changes in its characteristic properties upon contact with a detectable gas. The method includes coating an insulating substrate with an amorphous layer of a material constituting the gas-sensitive layer in a nano-size thickness; and rapidly heating the amorphous layer for its polycrystallization, thereby forming the gas-sensitive layer having as the main sensitive part a polycrystalline layer composed of a large number of uniform nano-size microcrystal grains which join together in the planar direction.

The term "nano-size" used in this specification typically means a size of several nanometers to tens of nanometers. It denotes the approximate thickness of the surface layer or several times in thickness. The surface layer is composed of the above-mentioned microcrystal grains which greatly change in their characteristic properties upon contact with a detectable gas. The term "main sensitive part" denotes that part or region of the gas-sensitive layer which profoundly affects the above-mentioned characteristic properties. This means that the main part excludes any fine particles it might contain if the gas-sensitive layer is to change in electric conductivity but the fine particles have nothing to do with the electric conductivity of the gas-sensitive layer.

The gas sensor according to one embodiment is one which has a gas-sensitive layer which changes in its characteristic properties upon contact with a detectable gas. The gas-sensitive layer has a main sensitive part which is a polycrystalline layer composed of a large number of uniform nano-size microcrystal grains which join together in the planar direction.

The above-mentioned nano-size microcrystal grains have a large ratio of surface area. This means that their change in characteristic properties takes place upon contact with a detectable gas mostly in their surface layer but little in their bulk layer. The microcrystal grains join together at their grain boundary through the surface layer as mentioned above. Therefore, the grain boundary changes in characteristic properties as the detectable gas changes in concentration. The change in characteristic properties manifests itself as the change in grain boundary potential influential on conduction electrons passing through grain boundaries. Thus the grain boundaries play an essential part in the gas sensing function and the main sensitive part of the gas-sensitive layer has a large number of such grain boundaries because it is composed of the microcrystal grains. Moreover, the grain boundary potential is uniform because the microcrystal grains and their grain boundaries are uniform in size and shape. The uniform grain boundaries produce the gas sensing function most effectively when the microcrystal grains have an adequate particle size. In other words, the maximum effect is obtained by selecting the microcrystal grains having an adequate particle size. Consequently, the main sensitive part of the gas-sensitive layer detects highly sensitively the change in concentration of the detectable gas in terms of the change in characteristic properties, such as electric conductivity.

Since the sensing function can be achieved so long as the nano-size microcrystal grains join together one- or two-dimensionally in the planar direction, the main part of the gas-sensitive layer can be formed from a monolayer in which there is only one grain in the thickness direction. The resulting gas sensor has a rapid sensing response because the main sensitive part of the gas-sensitive layer does not require the detectable gas to diffuse deep into it.

The gas sensor according to the embodiments operates stably at normal temperature because the gas-sensitive layer has a high gas sensitivity and does not require the detectable gas to diffuse deep into it. Consequently, it does not need a heater to promote reactions on the gas-sensitive layer or to cause the detectable gas to diffuse into the gas-sensitive layer. This leads to power saving, size reduction, and cost reduction.

The gas sensor according to embodiments is produced by a method including coating an insulating substrate with an amorphous layer of a material constituting the gas-sensitive layer in a nano-size thickness; and rapidly heating the amorphous layer for its polycrystallization, thereby forming the gas-sensitive layer having as the main sensitive part a polycrystalline layer composed of a large number of uniform nano-size microcrystal grains which join together in the planar direction.

An advantage of the production method mentioned above is that the main part of the gas-sensitive layer is prepared by polycrystallization of the amorphous layer. In this way it is possible to control the size of the microcrystal grains by properly selecting the thickness of the amorphous layer. Therefore, the main part of the gas-sensitive layer is easily formed in which a large number of uniform nano-size microcrystal grains join together in the planar direction. In addition, it may also be formed easily in the form of monolayer in which there is only one particle in the thickness direction. Since each step is simple and based on the known principle, the gas sensor can be produced easily, uniformly, and efficiently.

Additional features and advantages are described herein, and will be apparent from, the following Detailed Description and the figures.

DETAILED DESCRIPTION

Figure 1A:
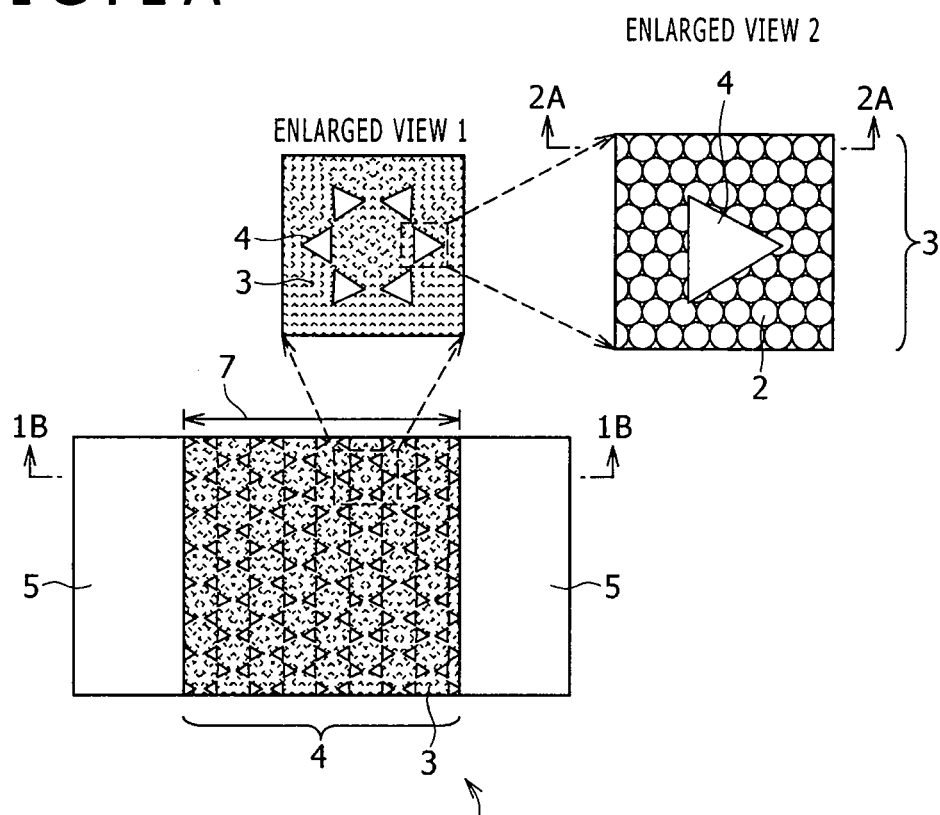
FIG. 1A is a top view and FIG. 1B is a sectional view each showing the structure of the main part of the gas sensor of metal oxide semiconductor according to the first embodiment.

The gas sensor according to embodiments should have the above-mentioned polycrystalline layer in the form of monolayer having only one particle in its thickness direction. With this structure, it does not require the detectable gas to diffuse deep inside the main part of the gas sensitive layer and hence it has a high response speed, as mentioned above. It also has another advantage of requiring no heating (by a heater) to help diffuse detectable gases. It follows from the foregoing that a highly sensitive and rapidly responsive gas sensor will be realized only by employing a gas sensitive layer of monolayer structure composed of nano-size microcrystal particles which are one- or two-dimensionally joined together in the planar direction.

The microcrystal particles should preferably be approximately spherical polyhedra having a shape such that the ratio of its diameter in the thickness direction to its diameter in the planar direction is from 0.8 to 1.2, more desirably from 0.95 to 1.05. With uniform size and nearly spherical shape, the microcrystal particles produce the uniform grain boundary potential desirable for the most effective gas sensing function. Accordingly, the optimum condition mentioned above easily leads the best effect. Moreover, the uniform particle size and the approximately spherical shape (indicated by the ratio close to 1) prove that the amorphous material has undergone uniform polycrystallization.

The gas-sensitive layer should have a thickness of 30 nm or smaller. This dimension corresponds to twice the thickness of the complete depletion layer of the crystalline material constituting the gas-sensitive layer because the microcrystalline particles constituting the monolayer have a particle diameter (in the thickness direction) equal to the thickness of the gas-sensitive layer. The microcrystalline particles have the surface layer only and do not have the bulk layer, and this contributes to the great sensitivity.

In addition, the gas-sensitive layer should have a thickness larger than 10 nm. This is because the microcrystalline particles with an excessively small size lose their electric properties as a semiconductor due to the unwanted quantum effect. Although the quantum effect varies depending on the material, crystallinity, temperature, and applied voltage, it will manifest itself even in particles with a diameter of about 10 nm when they are used at room temperature. The quantum effect shows up more easily as the operating temperature increases and the particle size decreases. Therefore, the gas-sensitive layer should have a thickness large enough to prevent the quantum effect (Coulomb blockage effect) at the operating temperature.

The gas-sensitive layer should have a surface with a belt-like or net-like pattern. The thus patterned surface has both its top and flank exposed to the detectable gas and hence makes the gas-sensitive layer more sensitive and responsive than the unpatterned surface without interstices. The net-like pattern should preferably be a honeycomb shape. The desired surface pattern will be formed easily by vacuum vapor deposition or sputtering through a mask (which is a mono-layer composed of two-dimensionally arranged fine particles in close-packed structure).

The gas-sensitive layer should be formed from a metal oxide semiconductor, which may be selected from a group consisting of tin (IV) oxide ($SnO_2$), zinc (II) oxide (ZnO), titanium (IV) oxide ($TiO_2$), indium (III) oxide ($In_2O_3$), vanadium (V) oxide ($V_2O_5$), tricobalt tetraoxide ($CO_3O_4$), and iron (III) oxide ($Fe_2O_3$). These materials should be properly selected according to the detectable gas. All of them are suitable for polycrystallization by rapid heating.

The microcrystalline particles of metal oxide semiconductor are mostly considered to form the double Schottky barrier at their grain boundary regardless of their grain size. This implies that two adjoining particles are definitely separated by a boundary and are mutually independent.

Figure 21:
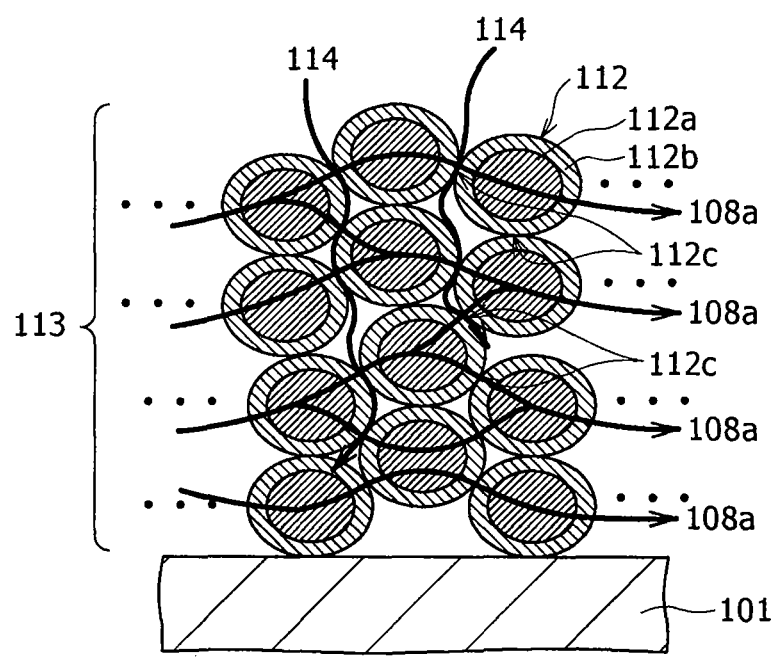
FIG. 21 is a schematic sectional view showing the gas-sensitive layer which is a polycrystal layer composed of a large number of microcrystals joining together.
Figure 22:
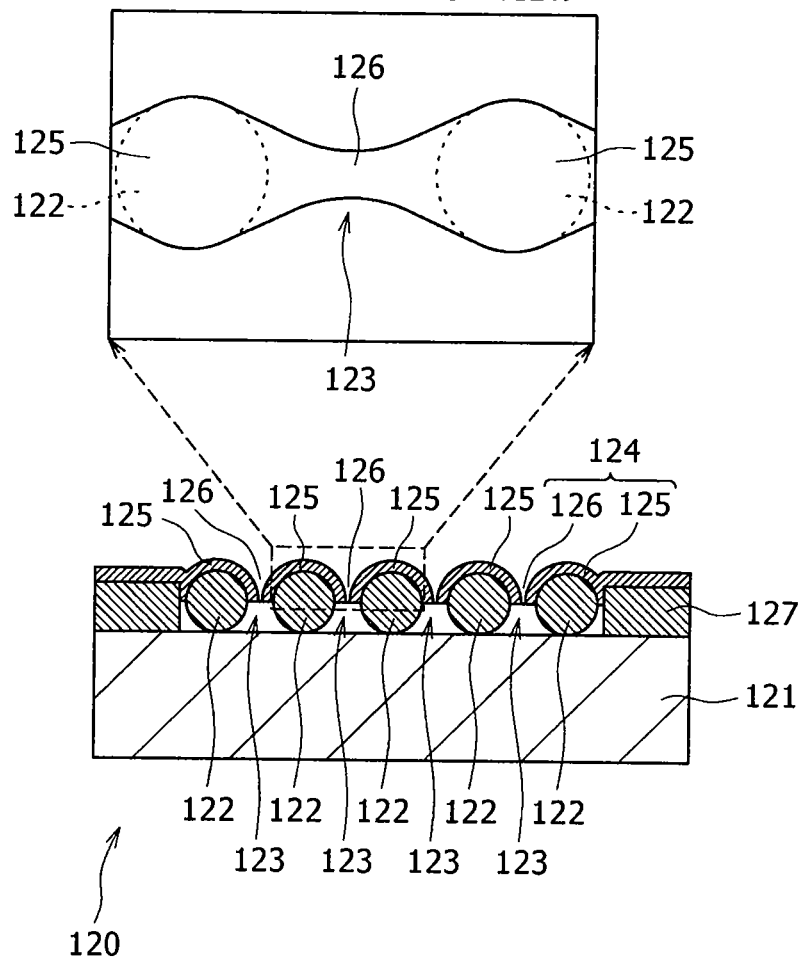
FIG. 22 is a partly enlarged top view and an enlarged sectional view showing the gas-sensitive layer (and its vicinity) disclosed in Japanese Patent Laid-open No. 2005-144569.
Figure 23:
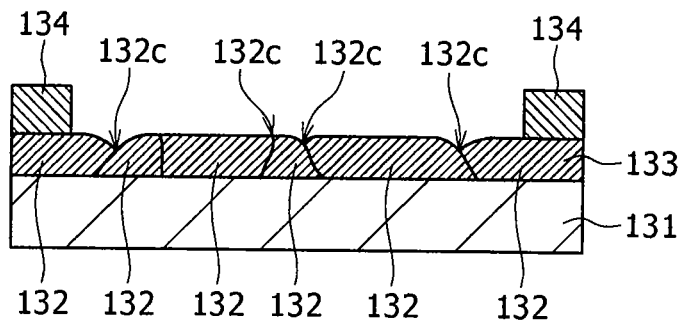
FIG. 23 is an enlarged sectional view showing the gas-sensitive layer (and its vicinity) disclosed in Japanese Patent Laid-open No. 2002-323467.

Ordinary polycrystals of metal or silicon do not form the barrier at their grain boundary. The fact that the microcrystalline particles of metal oxide semiconductor form the double Schottky barrier at their grain boundary is due to adsorption of gas (such as oxygen) to the grain surface near the grain boundary. Therefore, the double Schottky barrier varies in height upon contact with the detectable gas, and this causes the gas-sensitive layer to change in conductivity. Thus, the grain boundary potential, which changes upon contact with the detectable gas as mentioned above with reference to FIG. 21, plays an essentially important role for the sensing function of the polycrystalline gas-sensitive layer.

The gas-sensitive layer of microcrystalline particles in the gas sensor performs its gas sensing function in response to (1) the change in thickness of the surface depletion layer that occurs upon gas adsorption to the surface of the microcrystalline particles and (2) the change in barrier height that occurs upon gas adsorption in the neighborhood of the grain boundary. If the microcrystalline grains are in a thin long shape (like nano-wire), the second factor is not important because current flows mostly in the lengthwise direction of the microcrystalline grains. In this case, the gas-sensitive layer has a small resistance when it is not in contact with the detectable gas and it decreases in current only a little even when it comes into contact with the detectable gas.

By contrast, if the microcrystalline grains are in a nano-size spherical shape, the gas-sensitive layer has a large number of grain boundaries for current passage and hence those electrons passing through the gas-sensitive layer have to overcome a large number of barriers in the grain boundaries. Therefore, the gas-sensitive layer has a large resistance when it is not in contact with the detectable gas and it greatly decreases in resistance when it comes into contact with the detectable gas. This makes the gas sensor to improve in sensitivity and dynamic range. In fact, in the case of the gas sensor according to the embodiment mentioned later, the gas-sensitive layer has a very high resistance (more than 1000 times that of commercial ones) when it is not contact with the detectable gas.

The gas-sensitive layer should have a sensitizer (in contact therewith) consisting of a large number of discrete pieces. For its maximum effect, the sensitizer should have its individual pieces arranged in a lattice pattern with translational symmetry, such as honeycomb shape. The gas-sensitive layer with such a surface pattern will be formed easily by vacuum vapor deposition or sputtering through a mask (which is a monolayer composed of two-dimensionally arranged fine particles in close-packed structure), as mentioned above.

The sensitizer should preferably be a catalyst for the reaction that takes place on the surface of the gas-sensitive layer. The catalyst should contain at least one species of metallic element selected from the group consisting of platinum (Pt), palladium (Pd), silver (Ag), gold (Au), and ruthenium (Ru). The sensitizer may also be a receptor that adsorbs the detectable gas upon reaction with it or changes itself upon reaction with the detectable gas. (See Noboru Yamazoe, "The Transactions of the Institute of Electrical Engineers of Japan E", 115, p. 30 to 33 (1995), and Noboru Yamazoe, "Chemistry and Industry" 49, p. 1537 to 1539 (1996).)

The gas sensor according to the present invention works stably at normal temperature on account of its high performance gas-sensitive layer having the main part of mono-layer structure which does not require the detectable gas to diffuse deep thereinto. Therefore, it does not need any heater to promote the surface reaction on the gas-sensitive layer or to promote the diffusion of the detectable gas into the gas-sensitive layer. This leads to simple production steps, low power consumption, size reduction, and cost reduction.

The gas sensor having no heater will find more uses than the conventional ones which need heating. For example, it may be used as a methanol sensor for methanol fuel cells or as a bio-device in an environment where no heater can be used. It may also be applied to mobile equipment because of its low power consumption. It may be incorporated into an IC (integrated circuit) or LSI (large scale integration) when formed on a silicon substrate suitable for microfabrication.

The gas sensor according to the present invention will be used specifically for detecting alcohol, hydrogen, and combustible gas. It is useful as a sensor to detect humans (because it responds to expired gas) and chemical substances.

The method for producing the gas sensor according to the present invention should involve a step of rapid heating at a rate no lower than 100° C./s. Rapid heating in this manner polycrystallizes the amorphous layer uniformly, thereby forming the main part of the gas-sensitive layer which is composed of approximately spherical microcrystal grains. The heating rate (no lower than 100° C./s), which was employed in the embodiment mentioned later, may be increased for some materials in order to prevent the fusion of microcrystal grains.

The heating temperature should be higher than (or close to) the temperature at which the material constituting the amorphous layer crystallizes. The duration of heating should be long enough to form the microcrystal grains and short enough to prevent the fusion of the microcrystal grains. The heating temperature and the duration of heating are mutually related, and the higher the heating temperature, the shorter the duration of heating. If the amorphous layer is made of any of the materials listed in Table 1 (given later), the heating temperature should be 500° C. to 1500° C. and the duration of heating should be 10 seconds or shorter. In addition, the temperature and the duration of heating for crystallization vary depending on the atmosphere (such as air, oxygen, and nitrogen) in which heating is performed and also on the pressure of the atmosphere. Cooling may be accomplished by self-cooling or forced cooling, if necessary.

The amorphous layer should be formed by vacuum vapor deposition or sputtering, preferably by the PLD method (pulsed laser deposition), which readily gives a high-quality amorphous thin film having the same composition as the target used.

The amorphous layer, with a net-like surface pattern, should be formed by depositing the specified material through a mask composed of fine particles, which are two-dimensionally arranged with translational symmetry, with the incident angle (with respect to the insulating substrate) varied in a prescribed range.

Vacuum deposition or sputtering is a desirable method for forming the sensitizer on the gas-sensitive layer or amorphous layer in such a way that the sensitizer is divided into a large number of discrete fine pieces in a lattice pattern with translational symmetry.

This process may be accomplished by using a mask composed of fine particles which are two-dimensionally arranged with translational symmetry, with the incident angle (with respect to the insulating substrate) varied in a prescribed range.

The following is a detailed description of an embodiment which is shown in the accompanying drawings.

Embodiment 1

Figure 1B:
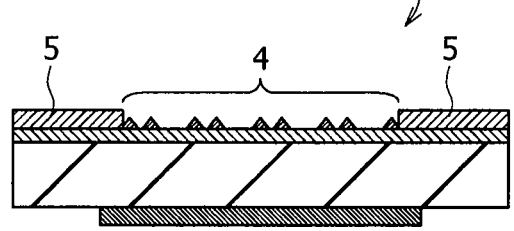

The gas sensor with metal oxide semiconductor according to Embodiment 1 has the main part 10 shown in FIGS. 1A and 1B, which includes a schematic top view (FIG. 1A) and a schematic sectional view (FIG. 1B) taken along the line 1B-1B in FIG. 1A. The main part 10 of the gas sensor with metal oxide semiconductor is composed of the insulating substrate 1 and the layer 3 of metal oxide semiconductor microcrystals formed thereon. This layer functions as the gas-sensitive layer which changes in its characteristic propertied upon contact with the detectable gas. It has the sensor region 7 formed at its center, with the sensitizer 4 uniformly distributed thereon. The sensor region 7 is held between the paired counter electrodes 5, which are in contact with the layer 3 of metal oxide semiconductor. The insulating substrate 1 has the thin-film heater 6 on its reverse side.

The main part 10 of the gas sensor is composed of the insulating substrate 1 and the layer 3 of metal oxide semiconductor covering the entire surface thereof. The latter has the sensor region 7, on which is the sensitizer 4 in the form of a large number of discrete particles uniformly distributed in a lattice pattern with translational symmetry. The sensitizer 4 shown in FIG. 1A is divided into discrete particles which are arranged in a honeycomb-like lattice pattern.

Figure 2A:
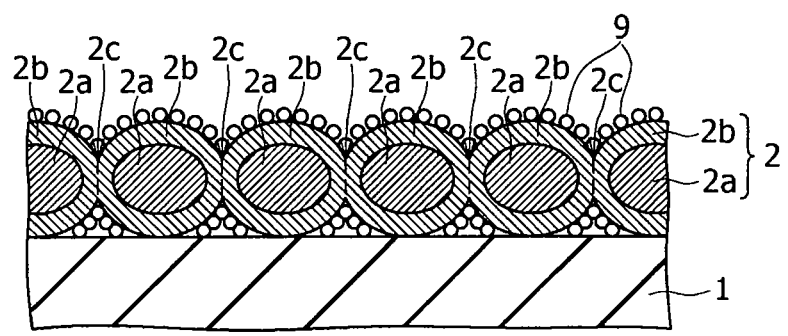
FIGS. 2A and 2B are sectional views each showing the microcrystal layer of metal oxide semiconductor in the main part of the gas sensor of metal oxide semiconductor according to the first embodiment.
Figure 2B:
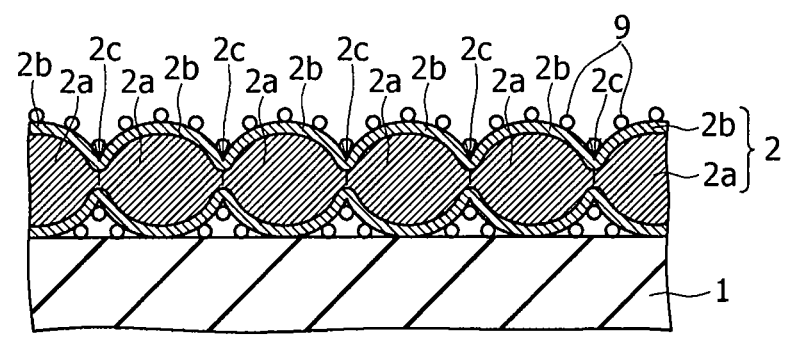

FIG. 1A includes the enlarged view 1 and the more enlarged view 2 in its supper part, which show the particles of the sensitizer 4. The sectional view taken along the line 2A-2A in the enlarged view 2 is shown in FIGS. 2A and 2B. It is to be noted from the enlarged view 2 and FIGS. 2A and 2B that the layer 3 of metal oxide semiconductor microcrystals is a mono-layer in which there exists only one microcrystal grain in the thickness direction. The mono-layer is composed of a large number of uniform, approximately spherical microcrystal grains 2 of metal oxide semiconductor, which are two-dimensionally arranged in the planar direction, with adjoining grains having the grain boundary 2c.

As mentioned above, the conduction electrons flowing through the layer 3 of metal oxide semiconductor always pass through the grain boundary 2c. The grain boundary 2c is where two microcrystal grains 2 come into contact with each other, with the surface depletion layer 2b interposed between them. Therefore, the grain boundary 2c changes in grain boundary potential as the detectable gas changes in concentration. The change in grain boundary potential affects the movement of the conduction electrons passing through the grain boundary 2c. Thus, the layer 3 of metal oxide semiconductor microcrystals owes its sensing function to the grain boundary potential. A highly sensitive gas sensor should be constructed such that conductivity through the grain boundary 2c greatly changes as the detectable gas changes in concentration.

FIGS. 2A and 2B show a preferred example of the gas sensor for reducing gases in which the metal oxide semiconductor constituting the layer 3 is tin (IV) oxide ($SnO_2$). As shown in FIG. 2A, the layer 3 of metal oxide semiconductor microcrystals placed in clean air fully adsorbs the oxygen molecules 9 on its surface. Therefore, the surface depletion layer 2b has the maximum thickness and the bulk layer 2a is divided into the individual microcrystal grains 2 of metal oxide semiconductor, which leads to a high resistance of the layer 3 of metal oxide semiconductor microcrystals. By contrast, as shown in FIG. 2B, the layer 3 of metal oxide semiconductor microcrystals placed in air containing a reducing gas loses part of the adsorbed oxygen molecules 9 from its surface on account of reactions between the adsorbed oxygen molecules 9 and the reducing gas. As the result, the surface depletion layer 2b decreases in thickness and the microcrystal grains 2 of metal oxide semiconductor constituting the bulk layer 2a join together, with the layer 3 of metal oxide semiconductor microcrystals greatly decreasing in resistance.

As shown in FIGS. 2A and 2B, the microcrystal grains 2 of metal oxide semiconductor are approximately spherical and have a particle diameter in the thickness direction and a particle diameter in the planar direction such that their ratio is from 0.8 to 1.2, preferably from 0.95 to 1.05. The uniform, approximately spherical microcrystal grains 2 give rise to the uniform grain boundaries 2c (and hence the uniform grain boundary potential) between the microcrystal grains 2. The uniform grain boundaries are essential for the gas sensing function. Therefore, the layer 3 of metal oxide semiconductor microcrystals is able to perform gas detection very sensitively as it changes in electrical conductivity in response to the change in concentration of the detectable gas. Moreover, the fact that the microcrystal grains 2 have a uniform, approximately spherical shape implies that the amorphous layer has undergone polycrystallization uniformly.

If the layer 3 of metal oxide semiconductor microcrystals is formed from tin (IV) oxide ($SnO_2$) or zinc (II) oxide (ZnO), the double Schottky barrier layer occurs in the grain boundary 2c. This indicates that the grains 2 of metal oxide semiconductor microcrystals form a clear boundary between adjoining ones and are almost independent from each other.

The highly sensitive structure shown in FIGS. 2A and 2B requires that the layer 3 of metal oxide semiconductor microcrystals should have a thickness smaller than 30 nm and larger than 10 nm. The thickness of 30 nm corresponds to twice the thickness of the complete depletion layer in the layer 3 of metal oxide semiconductor microcrystals. The foregoing requirement implies that the microcrystal grains 2 should have a particle diameter (not only in the thickness direction but also in the planar direction) smaller than 30 nm or smaller than twice the thickness of the complete depletion layer in view of the fact the layer 3 of metal oxide semiconductor microcrystals is a mono-layer and the microcrystal grains 2 are approximately spherical. The fact that the microcrystal grains 2 constitute only the surface layer but does not constitute the bulk layer is the reason for high sensitivity.

The layer 3 of metal oxide semiconductor microcrystals should be 10 nm or thicker. This is because it loses its semiconducting properties on account of the increasing quantum effect as it decreases in thickness (and hence the grain size becomes excessively small). It is impossible to strictly define the grain size small enough for the quantum effect which greatly depends on material, crystallinity, temperature, and voltage applied. The quantum effect easily occurs as the grain size decreases and it occurs at normal temperature when the grain size is about 10 nm. The grain size for the quantum effect decreases as the temperature rises. Consequently, the gas-sensitive layer should have an adequate thickness which suppresses the quantum effect (Coulomb blockage effect) according to the operating temperature.

For the gas-sensitive layer to perform its sensing function, it is only necessary that the nano-size microcrystal grains join together one- or two-dimensionally in the planar direction. Therefore, the main part of the gas-sensitive layer may be formed from a mono-layer in which there exists only one grain in the thickness direction. It makes the gas sensor highly responsive because it does not require the detectable gas to diffuse deep therein.

The insulating substrate 1 may be one which is formed from an oxide (such as alumina or aluminum oxide) or one which is composed of a substrate of semiconductor (such as silicon) and an insulating layer (of silicon nitride or the like) formed thereon. The counter electrodes 5 may be formed from any known conductive material.

Table 1 below shows the metal oxide semiconductors and the sensitizers (or the catalysts) combined therewith and the detectable gases to be sensed by them.

TABLE 1

| Semiconductor | Sensitizer | Detectable gas |
|---|---|---|
| $TiO_2$ | None | $O_2$ |
| $SnO_2$ | Pt, Pd, Ag | $H_2$, CO, methanol, ethanol, combustible gas |
| $Fe_2O_3$ | | $H_2$, methane, combustible gas |
| $Co_3O_4$ | Au | CO |

TABLE 1-continued

| Semiconductor | Sensitizer | Detectable gas |
|---|---|---|
| $V_2O_5$ | Ag | $NO_2$ |
| $WO_3$, $SnO_2$—$WO_3$ | | Trimethylamine (malodorous gas of N-containing compound), $NO_2$ |
| $In_2O_3$ | None | $Cl_2$ |
| CuO—$In_2O_3$ | None | Organochlorine compound (soil contaminant) |
| ZnO + $V_2O_5$ + $MoO_3$ | | Halogenated hydrocarbon |
| $ZnSb_2O_6$ | | $H_2S$, $CH_3SH$ (malodorous gas of S-containing compound) |
| $Ag_2O$ | None | Mercaptan |

The material for the layer 3 of metal oxide semiconductor microcrystals may be one which contains as the parent phase at least one metal oxide selected from the group consisting of tin (IV) oxide ($SnO_2$), zinc (II) oxide (ZnO), titanium (IV) oxide ($TiO_2$), indium (III) oxide ($In_2O_3$), vanadium (V) oxide ($V_2O_5$), tricobalt tetraoxide ($CO_3O_4$), and iron (III) oxide ($Fe_2O_3$).

The material for the sensitizer 4 should be one which contains at least one element selected from the group consisting of platinum (Pt), palladium (Pd), silver (Ag), gold (Au), and ruthenium (Ru). The sensitizer 4 is a catalyst for the reaction that takes place on the surface of the layer 3 of metal oxide semiconductor microcrystals.

The combination of ZnO+$V_2O_5$+$MoO_3$ shown in Table 1 functions as both the semiconductor and the sensitizer. These compounds may be mixed together or formed into a laminate to make a special sensor having a high response speed or suitable for a specific gas. The term "parent phase" used above denotes the composite structure of these compounds. The composite structure may also be obtained from the combination of $SnO_2$+ZnO or $SnO_2$+$WO_3$ (shown in Table 1). It will help improve the characteristic properties of the existing gas sensor or develop new gas sensors.

The layer 3 of metal oxide semiconductor microcrystals is connected in series to a current-detecting resistance and a circuit power source (both not shown) through the counter electrodes 5, so that the current flowing through it is measured in terms of output voltage across the terminals of the current-detecting resistance.

The concentration of the detectable gas is calculated by comparison between two values of electrical resistance of the layer 3 of metal oxide semiconductor microcrystals measured in clean air and in an atmosphere containing the detectable gas. During measurement, the layer 3 of metal oxide semiconductor microcrystals is heated to a prescribed temperature by the thin-film heater 6 and the voltage across the counter electrodes 5 is set up at a prescribed value.

Figure 3:
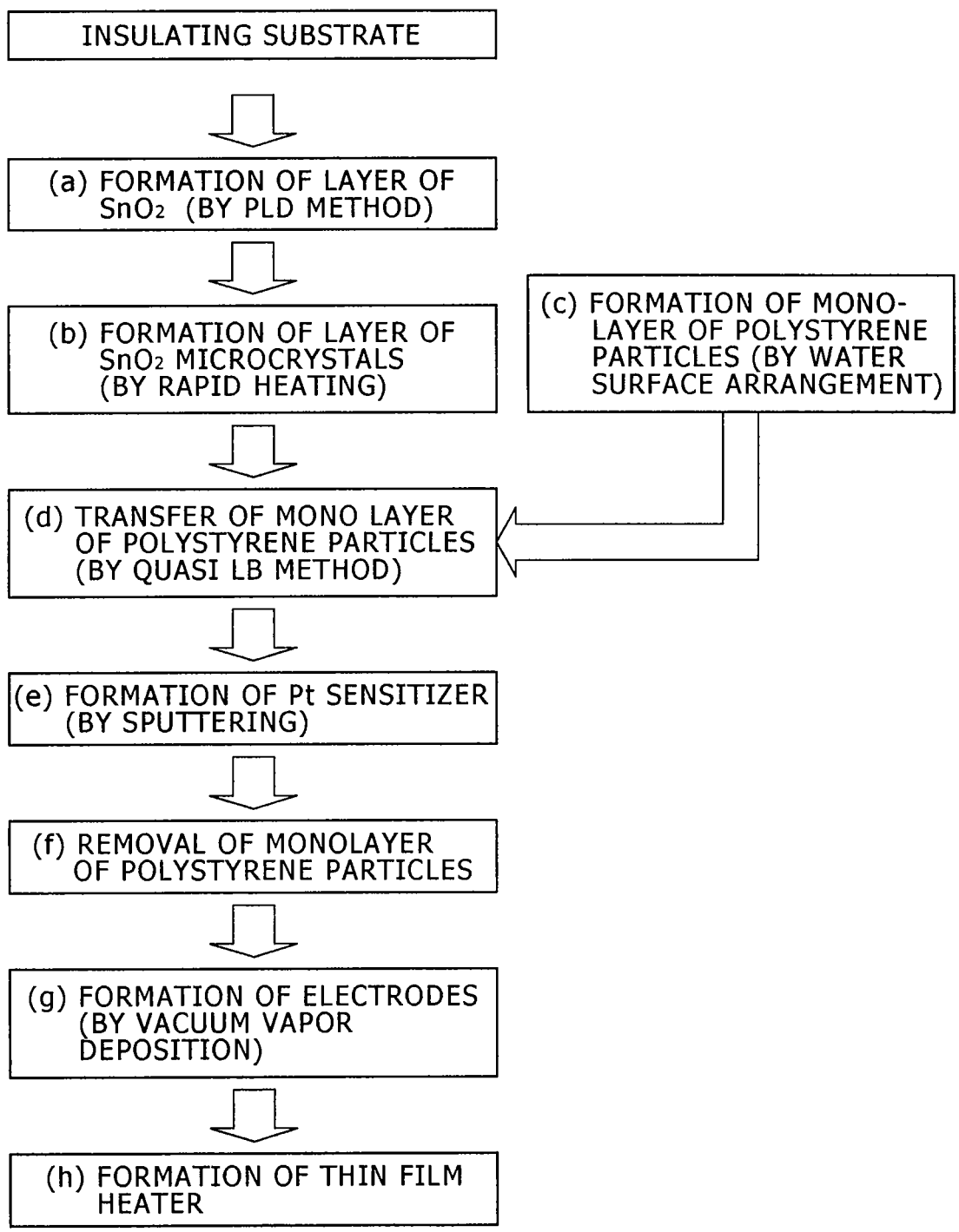
FIG. 3 is a flow sheet showing the process of producing the main part of the gas sensor of metal oxide semiconductor according to the first embodiment.

FIG. 3 is a flow sheet showing the process of producing the main part 10 of the gas sensor of metal oxide semiconductor according to Embodiment 1 of the present invention. FIGS. 4A to 4F are top views and sectional views showing the process of producing the main part 10 of the gas sensor of metal oxide semiconductor according to Embodiment 1 of the present invention. The steps (a) to (h) shown in FIG. 3 correspond to the steps (a) to (h) shown in FIGS. 4A to 4F. The sectional views in FIGS. 4A to 4F show the cross section at the same position as in FIG. 1B or the cross section taken along the line 4C-4C in FIG. 4B.

Figure 4A:
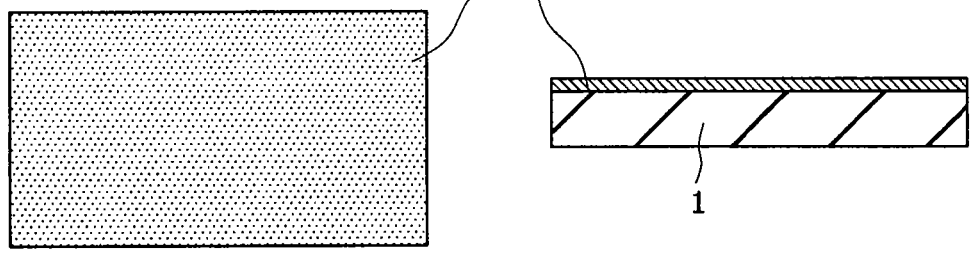
FIGS. 4A to 4F are each a sectional view and a top view showing the process of producing the main part of the gas sensor of metal oxide semiconductor according to the first embodiment.

The steps (a, b) shown in FIG. 4A are to coat the insulating substrate 1 with the layer 11 of amorphous metal oxide semiconductor (10 to 30 nm thick) by pulsed laser deposition (PLD method) at normal temperature. The PLD method employs incident high-energy laser beams to dissociate a target substance for deposition on the substrate. It readily gives a thin film of high crystal quality having the same composition as the target. Moreover, it takes no time for adjustment of composition unlike the sputtering method or molecular beam epitaxy (MBE) method.

The target used for the PLD method is a sintered body of tin oxide, which is formed from tin (IV) oxide ($SnO_2$) powder having a purity of 99.99% and ethanol (as a binder) by compression and ensuing heat treatment (for sintering) at 1300° C. for 30 hours.

The amorphous layer 11 deposited on the substrate is polycrystallized by rapid heating to form the layer 3 of metal oxide semiconductor microcrystals. The rapid heating is accomplished at a heating rate of 100° C./s and at not lower than 500° C. by using an electric furnace, infrared lamp furnace, or laser furnace.

Polycrystallization by rapid heating is easily applied to any one of the metal oxide semiconductors selected from the group consisting of tin (IV) oxide ($SnO_2$), zinc (II) oxide (ZnO), titanium (IV) oxide ($TiO_2$), indium (III) oxide ($In_2O_3$), vanadium (V) oxide ($V_2O_5$), tricobalt tetraoxide ($CO_3O_4$), and iron (III) oxide ($Fe_2O_3$).

Figure 5A:
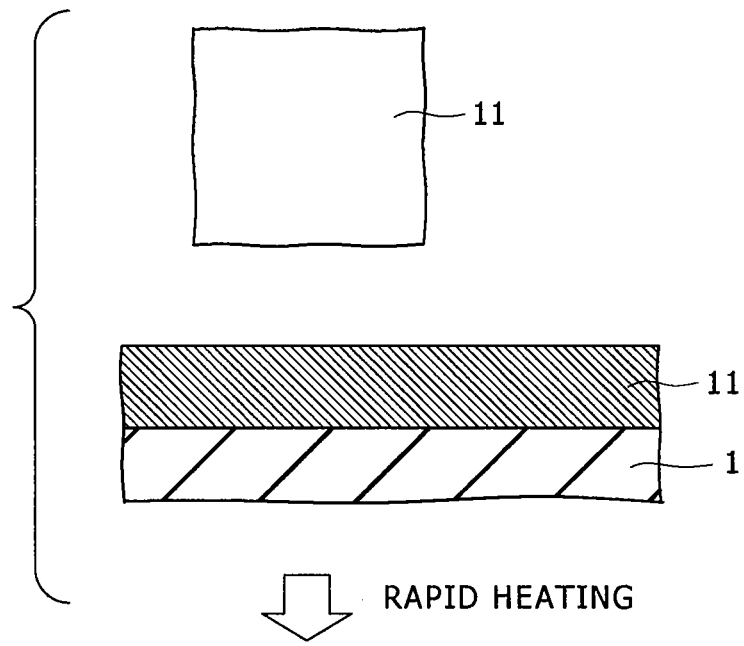
FIGS. 5A and 5B are each a top view and a sectional view illustrating the step of polycrystallization of the amorphous layer by rapid heating according to the first embodiment.
Figure 5B:
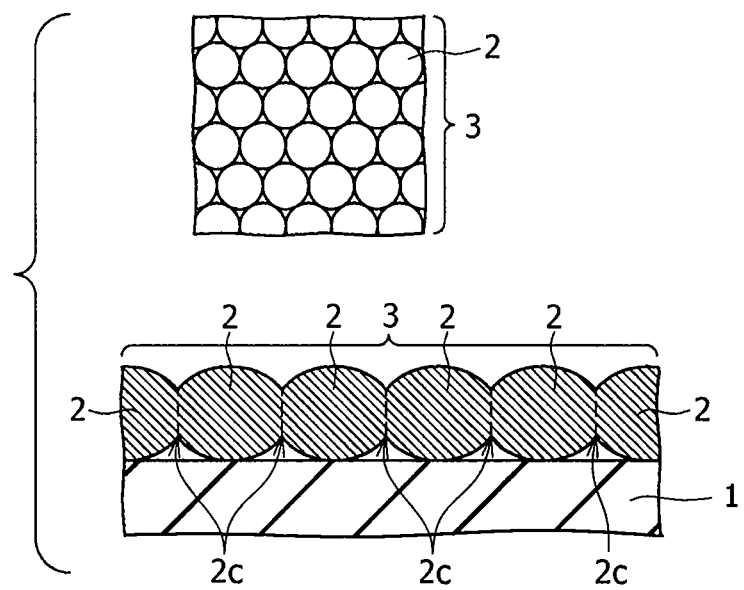

FIGS. 5A and 5B are a top view and a sectional view illustrating the step of polycrystallization of the amorphous layer 11 by rapid heating. The sectional view has a larger scale than the top view. The layer 11 of metal oxide semiconductor shown in FIG. 5A is amorphous, forming a mass without structure. Upon rapid heating, the amorphous layer 11 becomes crystalline, giving rise to a large number of microcrystals. These microcrystals grow rapidly by coalescence, while keeping their approximately spherical shape. The crystal growth ceases when the particle diameter of individual crystal grains becomes as large as the thickness of the layer 11. In this way there is formed the layer 3 of metal oxide semiconductor microcrystals having the structure shown in FIGS. 2A and 2B.

Figure 6:
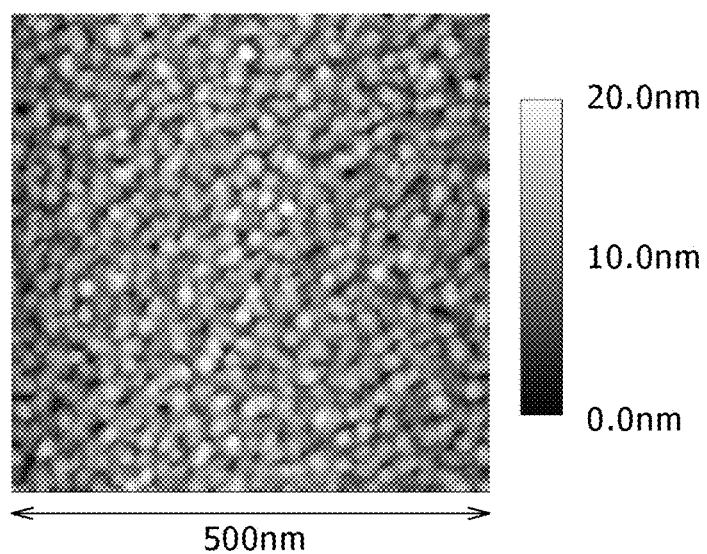
FIG. 6 is an atomic force microphotograph each showing the surface of the layer of metal oxide semiconductor microcrystals formed by rapid heating according to the first embodiment.

FIG. 6 is an atomic force microphotograph showing the surface of the layer 3 of metal oxide semiconductor microcrystals formed by rapid heat treatment on the amorphous layer 11 of tin oxide. It indicates that the metal oxide semiconductor microcrystal particle 2 has a width of 15 to 20 nm and a height of 15 to 20 nm. Incidentally, the photograph looks dark at its edges and convex at its center due to optical noises.

It is noted from FIG. 6 that polycrystallization by rapid heat treatment on the amorphous layer 11 forms uniform, approximately spherical microcrystals 2 unlike natural crystallization. This proves that the amorphous layer 11 undergoes polycrystallization almost uniformly over the entire surface thereof, as illustrated in FIGS. 2A and 2B.

As the result of rapid heating, the metal oxide semiconductor microcrystal grains have a controlled size approximately equal to the thickness of the amorphous layer 11 of metal oxide semiconductor. Thus, the layer 3 of metal oxide semiconductor microcrystals will be composed of microcrystal grains having a particle diameter of 10 to 30 nm if it is formed from the layer 11 of metal oxide semiconductor having a thickness of 10 to 30 nm.

Figure 4B:
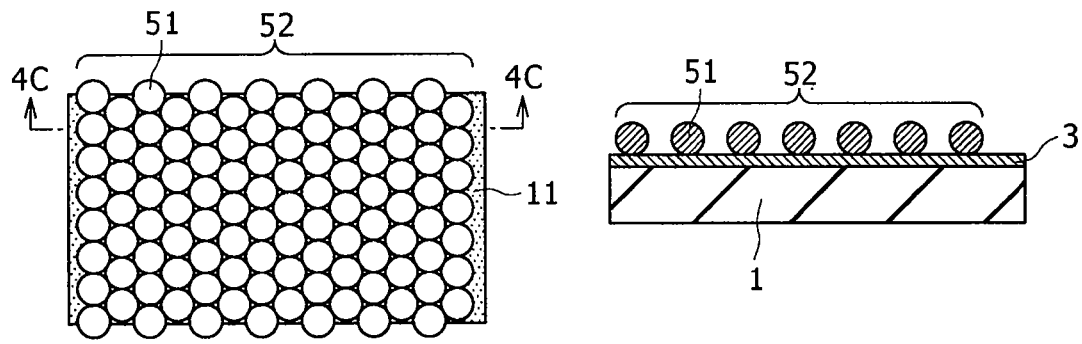

In the next steps (c, d) shown in FIG. 4B, the layer 3 of metal oxide semiconductor microcrystals is covered with the layer 52 of masking fine particles, in which the masking fine particles 51 are regularly arranged to form a mono-layer in close-packed structure by the water surface arrangement method and the quasi LB (Langmuir-Blodgette) method. The masking fine particles 51 may be fine particles of polystyrene or dielectric material (such as silicon oxide).

It is known that spherical fine particles of polystyrene align themselves to take on the close-packed structure. There has recently been reported a technology for arranging polystyrene fine particles in a single layer. The process employed in Embodiment 1 consists of a first step of forming a mono-layer of masking fine particles in close-packed structure on the water surface and a second step of transferring by the quasi LB method the mono-layer onto the layer 3 of metal oxide semiconductor microcrystals formed on the insulating substrate 1. The first step is the water surface arrangement method reported by A. Kosiorek et al., Nano Lett., 4, 1359 (2004).

FIGS. 7A to 7E illustrate the water surface arrangement method for making a mono-layer of polystyrene fine particles from a dispersion of polystyrene particles 51 in a 1:1 mixture of water and ethanol which is dropped on the water surface. The following mechanism may be assumed to explain how polystyrene particles form a mono-layer on the water surface.

Figure 7A:
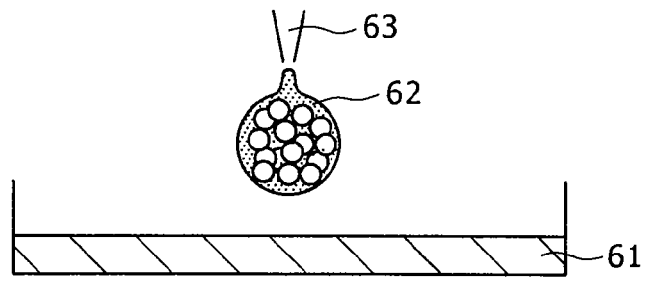
FIGS. 7A to 7E are sectional views each showing the step of forming the layer of masking fine particles by the water surface arrangement method and the quasi LB (Langmuir-Blodgette) method according to the first embodiment.
Figure 7B:
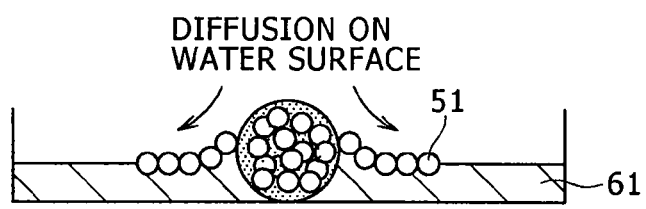
Figure 7C:
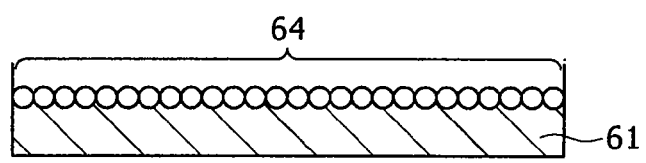
Figure 7D:
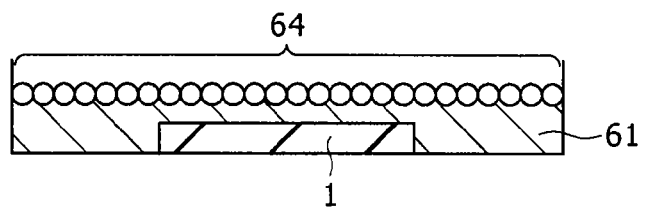

The first step is to drop the dispersion 62 of polystyrene fine particles 51 (in a water-ethanol mixture) on the surface of a small amount of water 61 from the pipette 63, as shown in FIG. 7A. The dropped dispersion 62 (which has a low surface tension) spreads over the water surface, as shown in FIG. 7B. The spread polystyrene particles remain in contact with one another, forming the mono-layer of close-packed structure on the water surface, as shown in FIG. 7C. The resulting layer 64 of polystyrene fine particles on the water surface takes on an opal-like interference color, which suggests the crystalline periodic arrangement of fine particles.

Figure 7E:
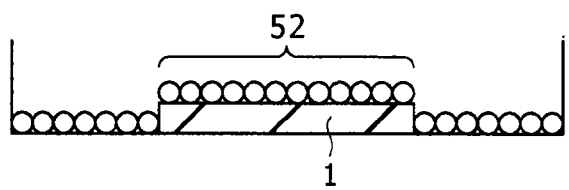

In the next step, the insulating substrate 1 is placed under the water layer 61, as shown in FIG. 8(d-1), and then the solvent is allowed to evaporate so that the layer 64 of polystyrene fine particles is transferred onto the insulating substrate 1, as shown in FIG. 7E.

Figure 4C:
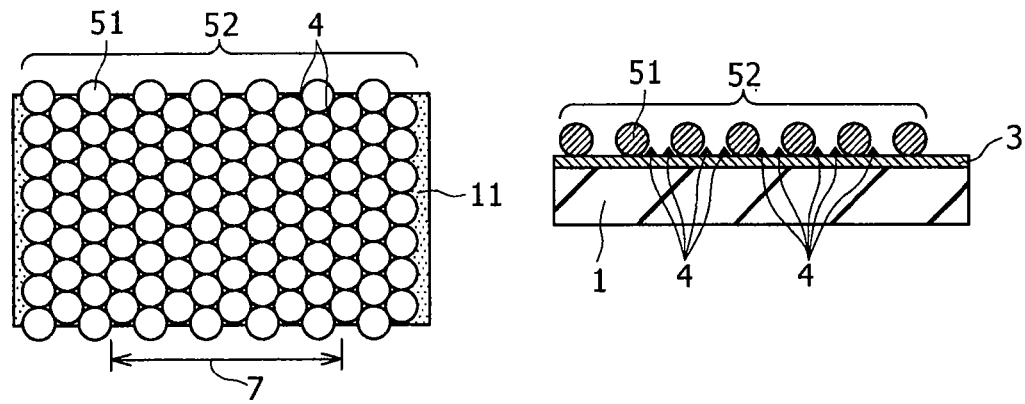

The transferred mono-layer 52 of polystyrene fine particles in close-packed structure is used as a mask for sputtering to form the sensitizer 4, such as platinum catalyst, consisting of discrete pieces, on the surface of the sensor region 7 at the center of the layer 3 of metal oxide semiconductor microcrystals, as shown in FIG. 4C.

Figure 8A:
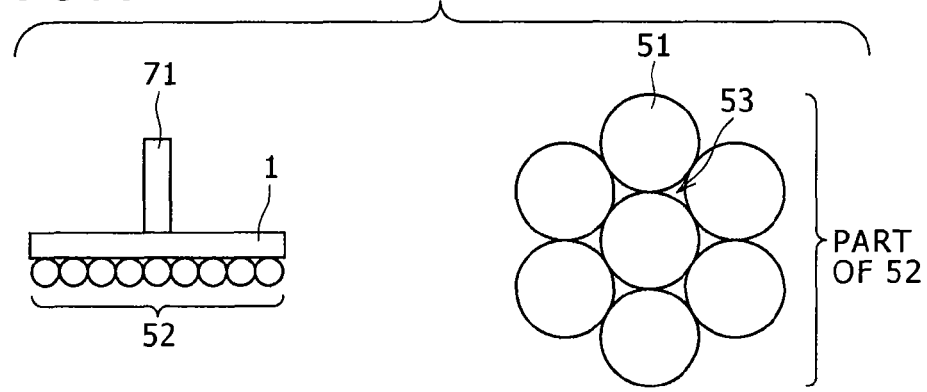
FIGS. 8A to 8C are diagrams each illustrating the sputtering method and PLD (pulsed laser deposition) method that use the layer of masking fine particles as a mask according to the first and second embodiments.
Figure 8B:
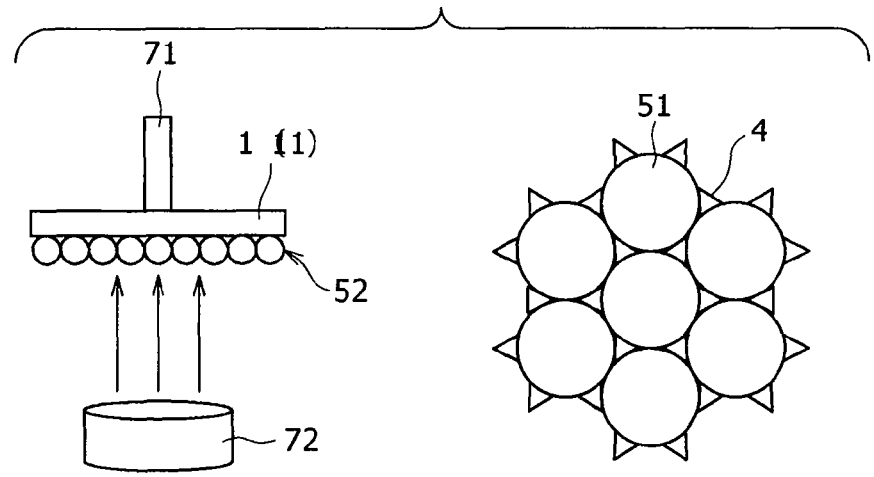
Figure 8C:
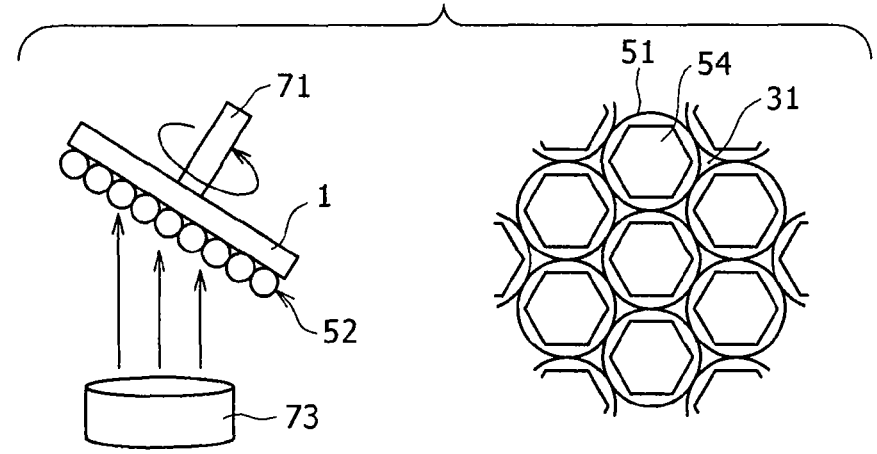
Figure 9A:
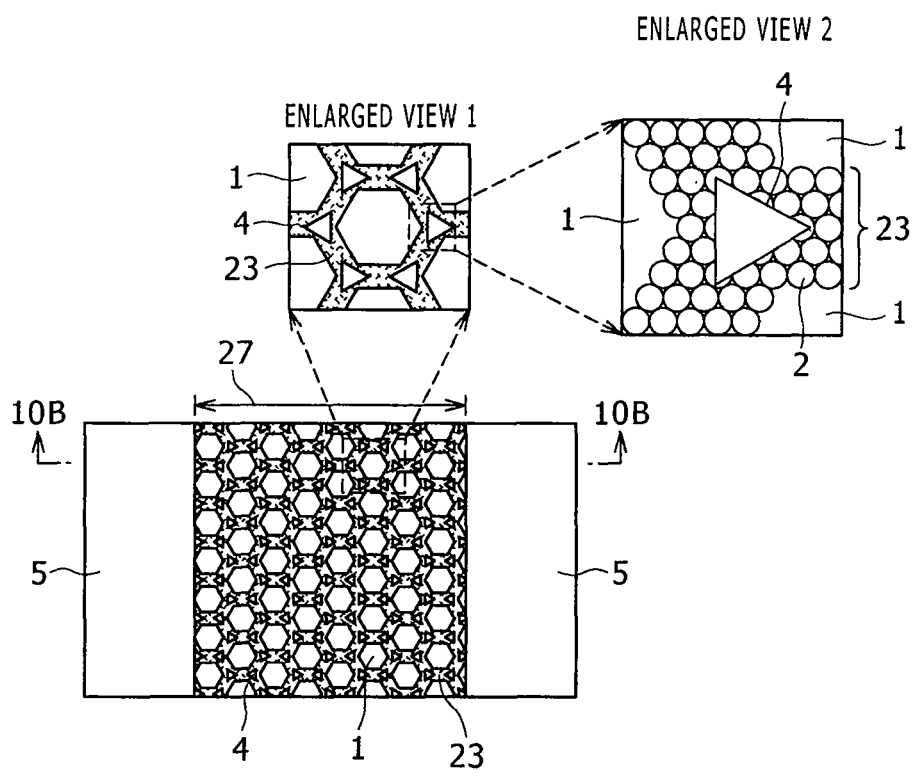
FIG. 9A is a top view and 9B is a sectional view each showing the structure of the main part of the gas sensor of metal oxide semiconductor according to the second embodiment.

FIGS. 8A to 8C illustrate the process of forming the sensitizer 4 consisting of discrete pieces by sputtering through the layer 52 of masking fine particles. The first step is to attach the insulating substrate 1 (with the mono-layer 52 of masking fine particles formed thereon) to the holder 71, as shown in FIG. 9(a). The diagram on the right is an enlarged top view of the mono-layer 52 of masking fine particles; it shows one central particle and its surrounding particles 51. It is noted that one central particle is surrounded by six particles 51 and has six interstices 53.

FIG. 8B illustrates the step of forming the sensitizer 4 consisting of discrete pieces. This step employs sputtering, with the target placed in front of the insulating substrate. Sputtering in this manner deposits the sensitizer 4 at the six interstices 53 around each masking fine particle 51, as shown in the diagram in the right. The resulting sensitizer 4 (which consists of discrete particles as a whole) takes on a honeycomb-like lattice pattern corresponding to the layer 52 of masking fine particles in close-packed structure. The diameter and pitch of the sensitizer 4 may be properly controlled by selecting an adequate diameter for the masking polystyrene fine particles 51.

Sputtering in the foregoing step should be carried out, with the holder 71 so positioned as to allow the insulating substrate 1 to face the target 72 accurately, so that the material for the sensitizer 4 is vertically incident on the insulating substrate 1 and the resulting sensitizer 4 consists of uniformly distributed discrete particles.

FIG. 8C illustrates the process of forming the layer of metal oxide semiconductor in a honeycomb net-like pattern by the PLD method which employs the layer 52 of masking fine particles in Embodiment 2 mentioned later.

Figure 4D:
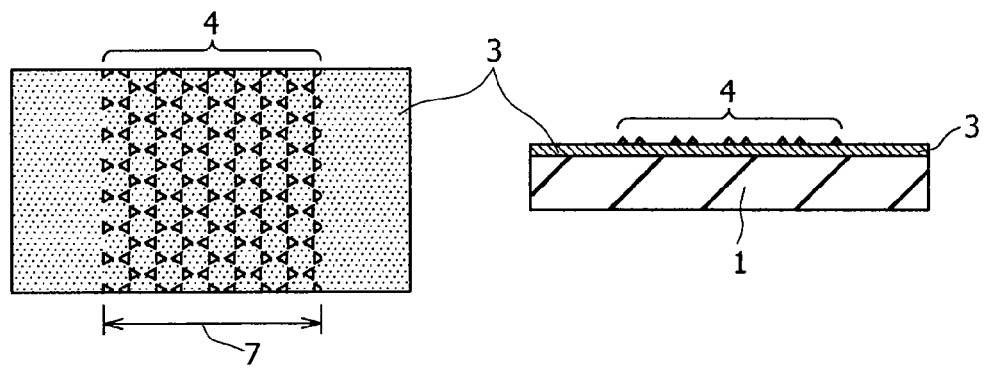

After the step (e) shown in FIG. 4C, the layer 52 of polystyrene masking fine particles is removed by dissolution in toluene, as shown in step (f) in FIG. 4D.

Figure 4E:
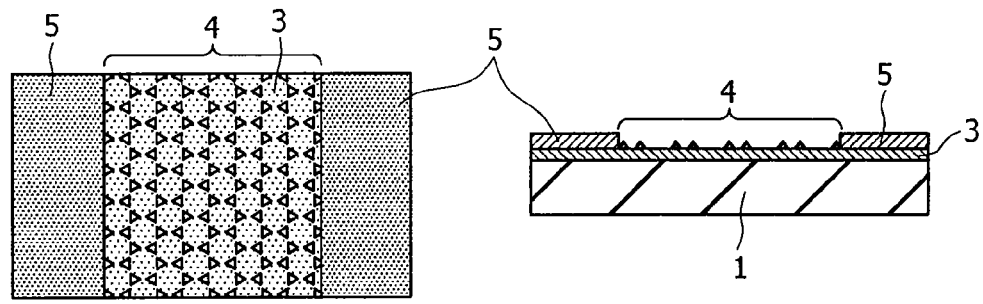

The layer 3 of metal oxide semiconductor microcrystals is directly provided with the counter electrodes 5 of conducting material at their both ends holding the sensor region 7 between them, as shown in step (g) in FIG. 4E.

Figure 4F:
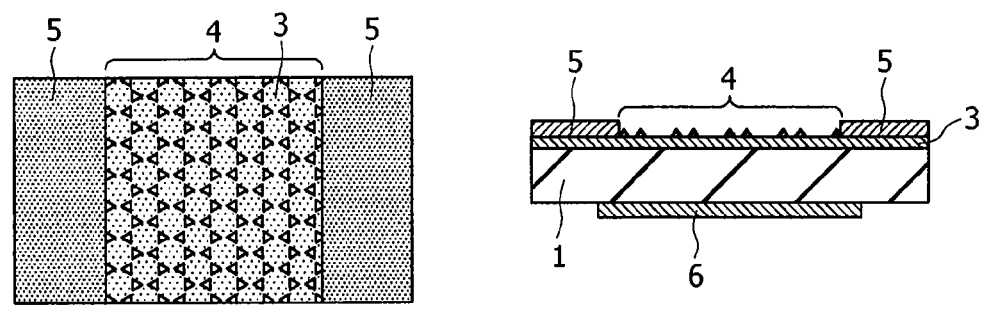

The insulating substrate 1 is provided with the thin-film heater 6 (of platinum or nichrome) on its reverse side, as shown in step (h) in FIG. 4F, and terminals and wiring connected to the heater 6 are formed.

Thus there is obtained the gas sensor of metal oxide semiconductor as desired.

Embodiment 2

Embodiment 2 is identical with Embodiment 1 except that the layer 23 of metal oxide semiconductor microcrystals (which is the gas-sensitive layer) has a honeycomb net-like pattern. The difference is described below.

Figure 9B:
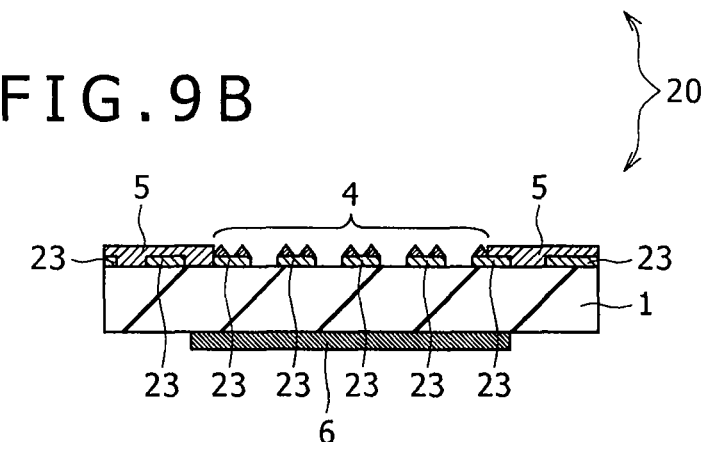

The gas sensor with metal oxide semiconductor according to Embodiment 2 has the main part 20 shown in FIGS. 9A and 9B, which includes a schematic top view (FIG. 9A) and a schematic sectional view (FIG. 9B) taken along the line 10B-10B in FIG. 9A. The main part 20 of the gas sensor with metal oxide semiconductor is composed of the insulating substrate 1 and the layer 23 of metal oxide semiconductor microcrystals formed thereon. This layer functions as the gas-sensitive layer which changes in its characteristic propertied upon contact with the detectable gas. It has at its center the sensor region 27 with a honeycomb net-like pattern. The sensor region 27 has the sensitizer 4 which is divided into discrete pieces, each positioned at the intersection of the net-like pattern. The sensor region 27 is held between the paired counter electrodes 5, which are in contact with the layer 23 of metal oxide semiconductor. The insulating substrate 1 has the thin-film heater 6 on its reverse side.

FIG. 9A includes the enlarged view 1 and the more enlarged view 2 in its upper part.

Embodiment 2 is characterized in that the layer 23 of metal oxide semiconductor microcrystals has a belt-like or net-like pattern, so that it is exposed to the detectable gas at its top as well as its side. Therefore, the result is a higher sensitivity and a greater response speed than that achieved by Embodiment 1 in which the layer 3 of metal oxide semiconductor microcrystals is densely formed on the entire surface. Moreover, the specific pattern restricts the path of current in the layer 23 of metal oxide semiconductor microcrystals to the region where the discrete pieces of the sensitizer 4 exist. This permits the sensitizer 4 to be used more effectively.

Figure 10:
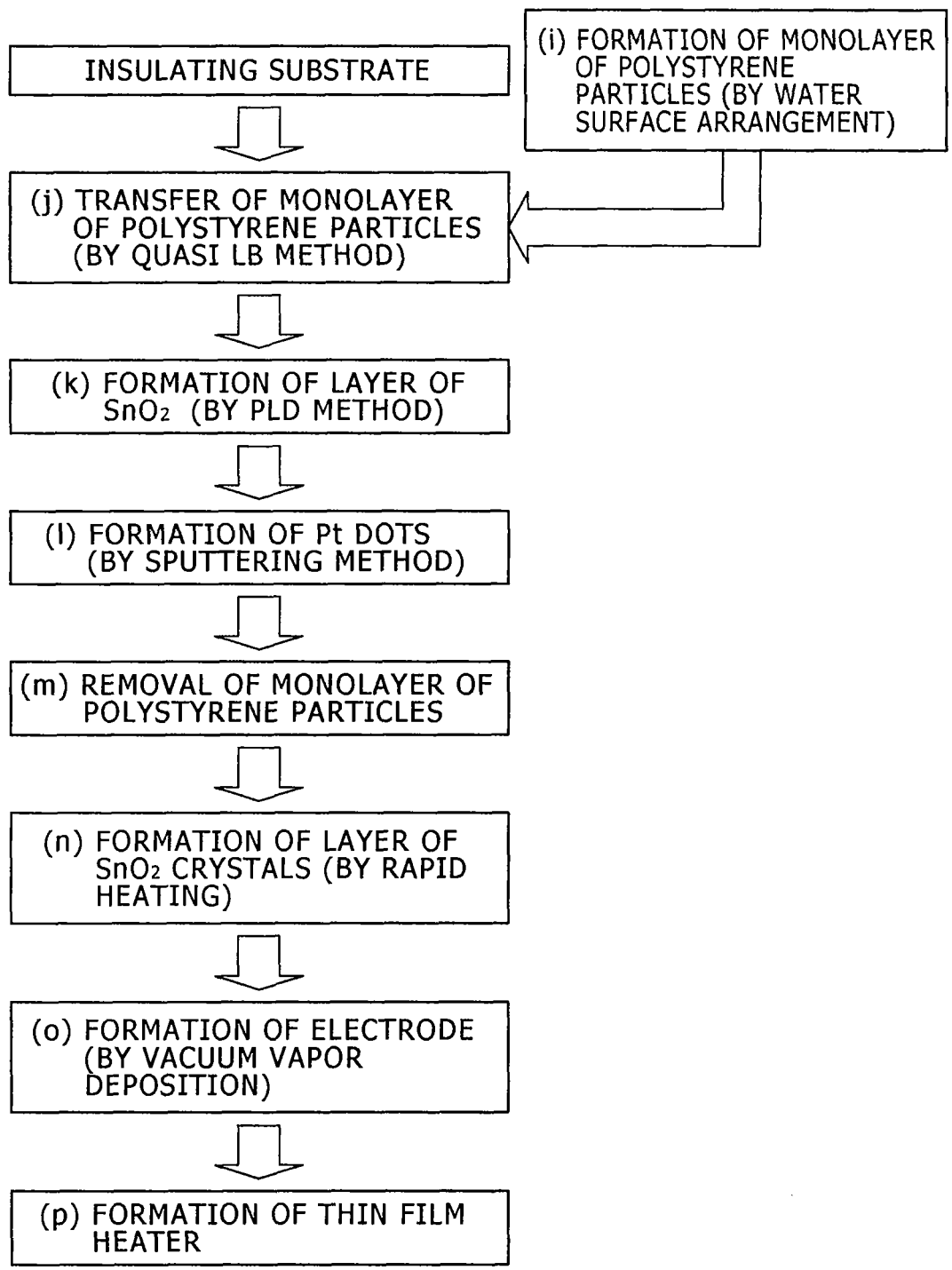
FIG. 10 is a flow sheet showing the process of producing the main part of the gas sensor of metal oxide semiconductor according to the second embodiment.

FIG. 10 is a flow sheet showing the process of producing the main part 20 of the gas sensor of metal oxide semiconductor according to Embodiment 2. FIGS. 11A to 11F are top views and sectional views showing the process of producing the main part 20 of the gas sensor of metal oxide semiconductor according to Embodiment 2. The steps (i) to (p) shown in FIG. 10 correspond to the steps (i) to (p) shown in FIGS. 11A to 11F. The sectional views in FIGS. 11A to 11F show the cross section at the same position as in FIG. 9B or the cross section taken along the line 12K-12K in FIG. 11B.

Figure 11A:
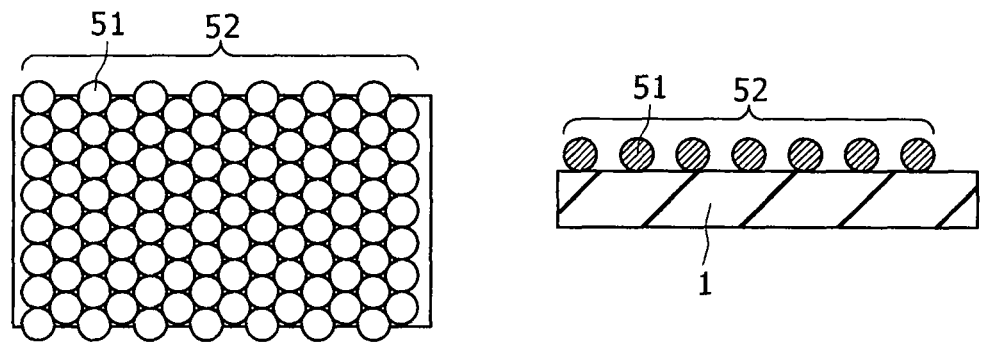
FIGS. 11A to 11F are each a top view and a sectional view showing the process of producing the main part of the gas sensor of metal oxide semiconductor according to the second embodiment.

In the steps (i, j) shown in FIG. 11A, the insulating substrate 1 is covered with the layer 52 of masking fine particles 51 (which is a mono-layer of close-packed structure), in the same way as shown in FIG. 4B. The masking fine particles 51 are regularly arranged by the water surface arrangement method and quasi LB method.

Figure 11B:
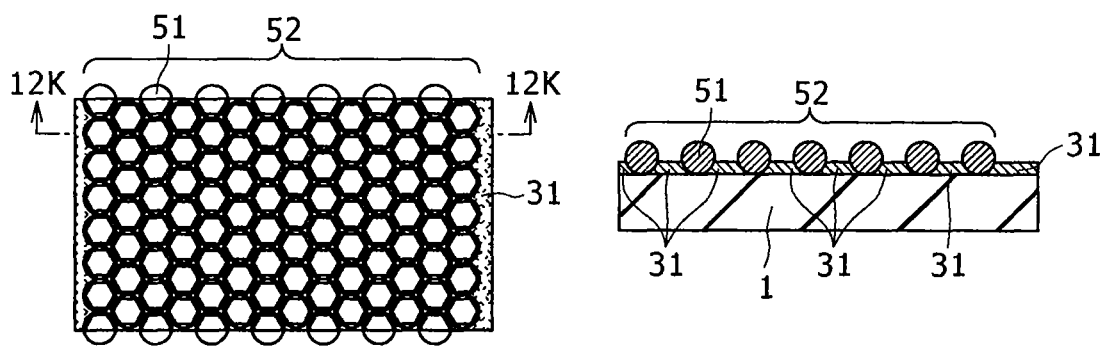

In the next step (k) in FIG. 11B, the insulating substrate 1 is coated with the layer 31 of amorphous metal oxide semiconductor material (10 to 30 nm thick) by the PLD method at normal temperature. This step employs as a mask the layer 52 of masking fine particles (which is a mono-layer of close-packed structure). The resulting coating film has a honeycomb net-like pattern.

FIG. 8C illustrates the step of forming the layer 31 of metal oxide semiconductor material (having a honeycomb net-like pattern) by the PLD method that employs as a mask the layer 52 of masking fine particles. The PLD deposition in this step is carried out in such a way that the target 73 is displaced from the front face of the insulating substrate 1 (and hence the holder 71 is inclined with respect to the target 73) and the metal oxide semiconductor material impinges upon the insulating substrate 1 at an angle deflected from the normal line by 10 to 45 degrees. Deposition in this manner makes the masked region 54 smaller than the circular region 51 which would be masked in the case of deposition in the vertical direction. Thus it is possible to form the layer 31 of metal oxide semiconductor material whose surface has a honeycomb net-like pattern. The pitch of the pattern may be controlled by adequately selecting the size of the polystyrene particles. The net-like pattern of the layer 31 of metal oxide semiconductor material consists of the circular units whose width may be properly controlled by selecting the size of the polystyrene particles and changing the incident angle. An adequate width is about 50 nm (which is large enough to contain 2 to 5 particles of the metal oxide semiconductor microcrystal having a grain size of about 10 to 15 nm).

Figure 11C:
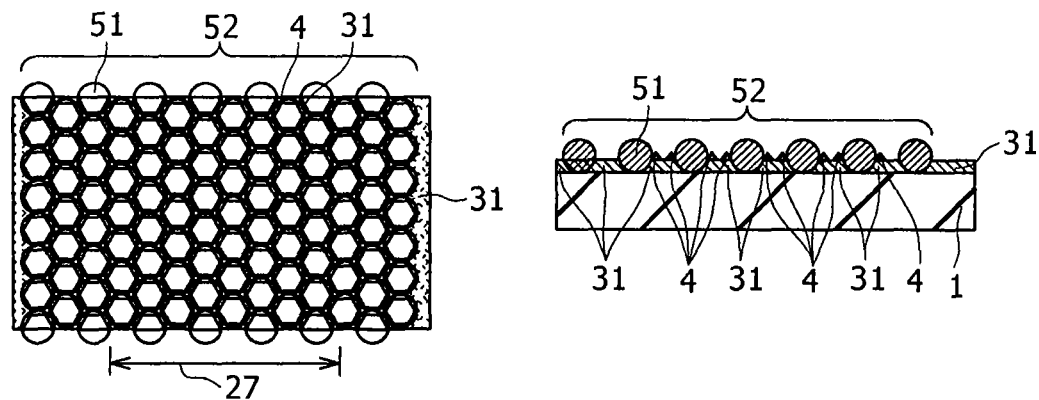

Next, the sensor region 27 at the center of the layer 31 of metal oxide semiconductor material undergoes sputtering through the layer 52 of masking fine particles as shown in FIG. 11C, in the same way as shown in FIG. 4C, so that the sensitizer 4 (of metal catalyst such as platinum) consisting of divided discrete pieces is formed. Sputtering in this manner accurately places the discrete pieces of the sensitizer 4 at the intersections of the honeycomb net-like pattern on the layer 31 of the metal oxide semiconductor material without mask displacement.

In this step, sputtering is carried out in such a way that the holder 71 is oriented to make the insulating substrate 1 face the target 72 at normal angle and the material of the sensitizer 4 vertically impinges upon the insulating substrate 1. Sputtering in this manner uniformly forms the sensitizer 4 divided into discrete pieces.

Figure 11D:
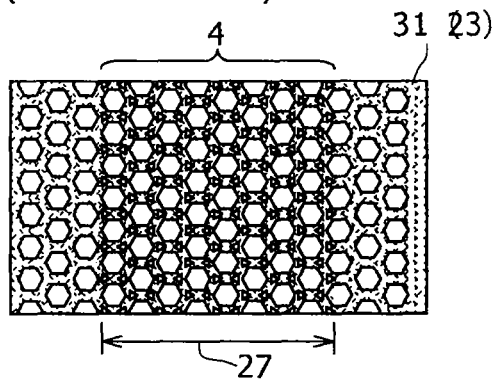
Figure 11D:
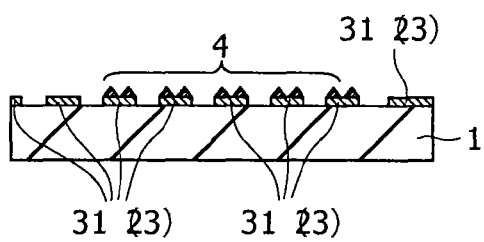

In the next steps (m, n) shown in FIG. 11D, the masking fine particles 52 of polystyrene are removed by dissolution in toluene in the same way as the step (f) shown in FIG. 4D. Subsequently, the layer 31 of metal oxide semiconductor material (which is an amorphous layer) undergoes rapid heat treatment for polycrystallization to form the layer 23 of metal oxide semiconductor microcrystals, in the same way as shown in step (b) in FIG. 4A.

Figure 11E:
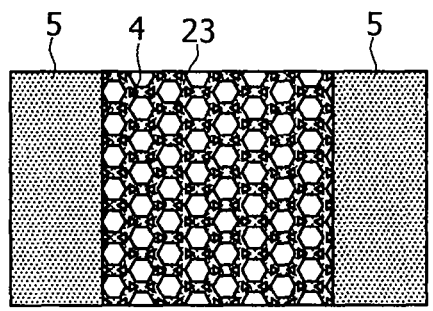
Figure 11E:
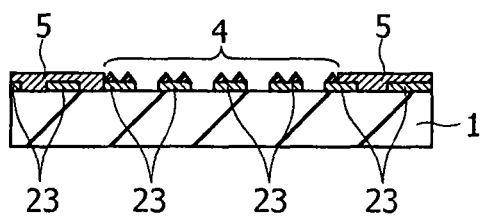

The layer 23 of metal oxide semiconductor microcrystals is provided directly with the counter electrodes 5 of conducting material at their both ends holding the sensor region 27 between them, as shown in step (O) in FIG. 11E, in the same way as shown in step (g) in FIG. 4E.

Figure 11F:
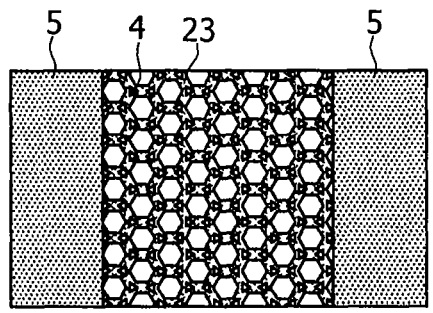
Figure 11F:
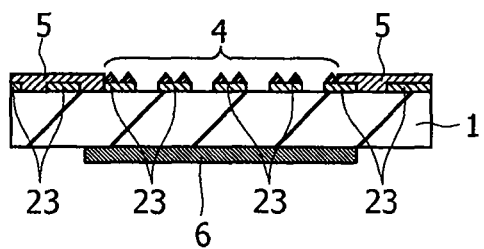

The insulating substrate 1 is provided with the thin-film heater 6 (of platinum or nichrome) on its reverse side, as shown in step (p) in FIG. 11F, and terminals and wiring connected to the heater 6 are formed, in the same way as shown in step (h) in FIG. 4F.

Thus there is obtained the gas sensor 20 of metal oxide semiconductor as desired.

An alternative method may be used to prepare the layer 23 of metal oxide semiconductor microcrystals. It consists of the first step of coating the entire surface of the insulating substrate 1 with the layer 11 of metal oxide semiconductor material and the second step of patterning the layer 11 by dry etching or wet etching through a mask composed of dielectric fine particles or thin wire structure formed therefrom.

Figure 12:
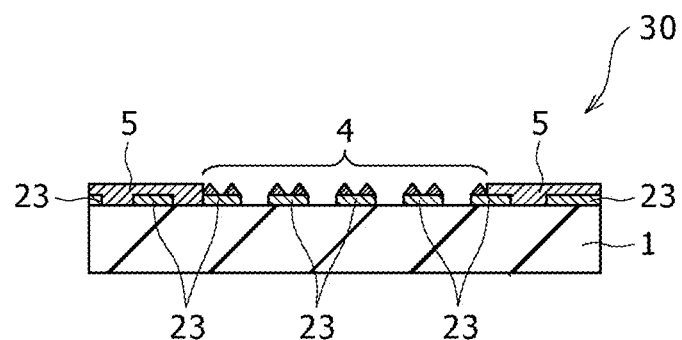
FIG. 12 is a sectional view showing the structure of the main part of the gas sensor of metal oxide semiconductor that operates at normal temperature according to the modified second embodiment.

FIG. 12 is a sectional view showing the structure of the main part 30 of the gas sensor of metal oxide semiconductor according to Embodiment 2 modified. The main part 30 differs from the main part 20 in having the thin film heater 6 eliminated, so that the gas sensor with it operates at normal temperature.

The gas sensor constructed as mentioned above saves power consumption because it has no heater, and it also permits size reduction and process simplification.

EXAMPLE

This example is intended to prepare a gas sensor having the main part 30 shown in Embodiment 2 modified, in which the metal oxide semiconductor material is $SnO_2$. The gas sensor was examined for gas detecting characteristics at normal temperature. Incidentally, $SnO_2$ is a well-known long-proven metal oxide semiconductor; it is chemically stable and practically useful as a sensor material.

Preparation of the Main Part 30 of the Gas Sensor

The process for preparing the main part 30 of the gas sensor of metal oxide semiconductor will be described below step by step. The steps (i) to (O) mentioned in the following correspond to the steps (i) to (O) mentioned above with reference to FIGS. 10 to 11F.

<Steps (i) and (j)>

Figure 13:
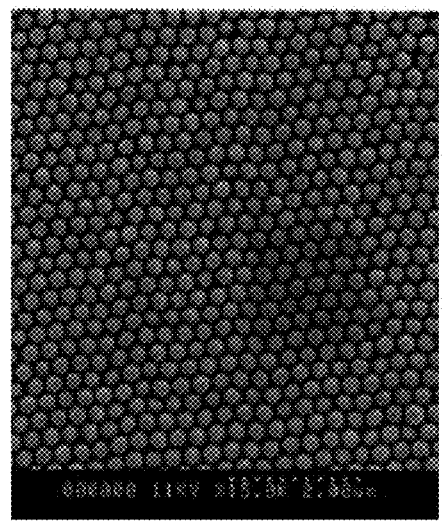
FIG. 13 is an electron micrograph showing the layer of masking polystyrene fine particles used in one example.

The silicon insulating substrate 1 with a surface coating of silicon oxide ($SiO_2$) is covered with the layer 52 of masking fine particles (or polystyrene fine particles having a particle diameter of 300 nm) by the water surface arrangement method and quasi LB method. FIG. 13 is an electron micrograph showing the layer of masking polystyrene fine particles. It is noted that the polystyrene fine particles are two-dimensionally arranged.

<Step (k)>

On the insulating substrate 1 is formed the layer 31 of metal oxide semiconductor ($SnO_2$), which has a honeycomb pattern, by the PLD method at normal temperature through the layer 52 of masking fine particles as the mask. The PLD deposition in this step is carried out in such a way that the metal oxide semiconductor material impinges upon the insulating substrate 1 at an angle deflected from the normal line by 10 to 45 degrees. Deposition was continued until the layer thickness reached 10 nm.

<Step (l)>

On the layer 31 of metal oxide semiconductor is formed the sensitizer 4 of platinum (Pt), which is divided into discrete pieces, by sputtering at normal temperature through the layer 52 of masking fine particles as the mask, in the same way as in the step (k). The incident angle for platinum was kept vertical with respect to the insulating substrate 1. The discrete pieces of the sensitizer 4 have a particle diameter of 50 nm.

<Step (m)>

Figure 14:
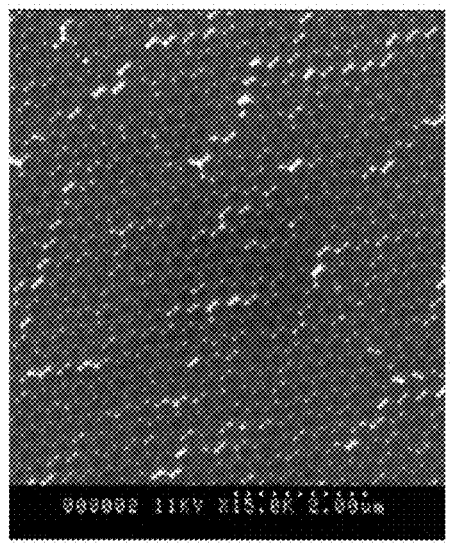
FIG. 14 is an electron micrograph showing the surface of the insulating substrate which has passed the step (m) in one example.

The layer 52 of masking fine particles (polystyrene fine particles) was removed by dissolution in toluene. FIG. 14 is an electron micrograph showing the surface of the insulating substrate 1 after this step. It is noted that the honeycomb pattern on the surface consists of the layer 31 of amorphous metal oxide semiconductor material (SnO$_2$), which has a high areal ratio and a high density, and the sensitizer 4 of platinum, which is divided into discrete pieces at the intersections of the honeycomb pattern.

<Step (n)>

Figure 15:
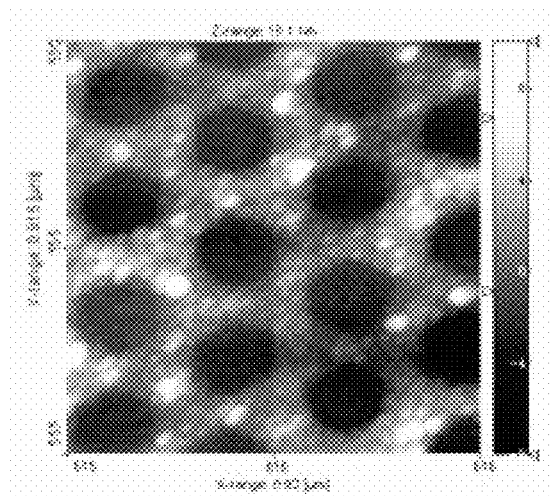
FIG. 15 is an atomic force microphotograph showing the surface of the insulating substrate which has passed the step (n) in one example.

The coated insulating substrate undergoes rapid heating (at a rate of 100° C./s) in an infrared lamp furnace. FIG. 15 is an atomic force microphotograph showing the surface of the thus processed insulating substrate 1. It is noted that the honeycomb pattern on the surface consists of the layer 31 of metal oxide semiconductor material (SnO$_2$), which has a high areal ratio and a high density, and the sensitizer 4 of platinum, which is divided into discrete pieces at the intersections of the honeycomb pattern.

<Step (o)>

The layer 23 of metal oxide semiconductor microcrystals is provided directly with the counter electrodes 5 of gold (Au) at their both ends holding the sensor region 27 between them. The counter electrodes 5 are 10 μm apart.

Thus there is obtained the main part 30 of the gas sensor of metal oxide semiconductor capable of operation at normal temperature, as shown in FIG. 12.

Gas detecting characteristics at normal temperature

The gas sensor obtained by the above-mentioned steps is examined for methanol gas detecting characteristics at normal temperature. Gas detection is confirmed by measuring the change in current flowing through the layer 23 of the metal oxide semiconductor microcrystals of the gas sensor 30 placed in a closed chamber into which methanol gas is introduced.

Figure 16:
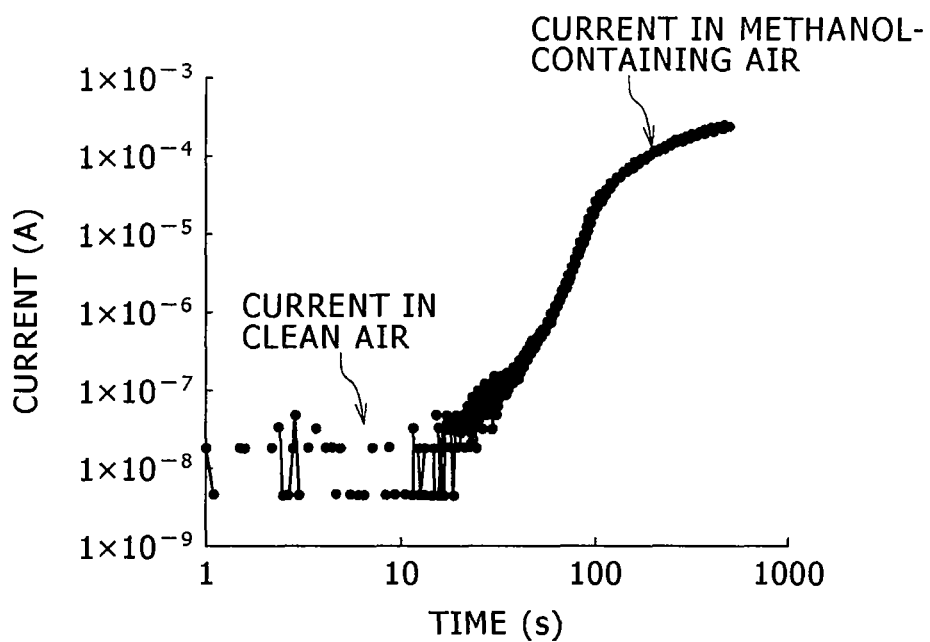
FIG. 16 is a graph showing how the gas sensor of metal oxide semiconductor (in one example of the present invention) changes in its output current as it detects methanol at normal temperature.

FIG. 16 is a graph showing how the gas sensor 30 of metal oxide semiconductor changes in its output current as it detects methanol at normal temperature. It is noted that the current flowing through the layer 23 of metal oxide semiconductor microcrystals in a methanol-containing atmosphere is about four order of magnitude larger than that in clean air even at normal temperature.

This results suggests that the gas sensor 30 of metal oxide semiconductor has an enhanced sensitivity (or surface gas reactivity) owing to the layer 23 of metal oxide semiconductor microcrystals in a honeycomb pattern having a high areal ratio and a high density and the sensitizer 4 of platinum which has the two-dimensional nano-structure.

Figure 17:
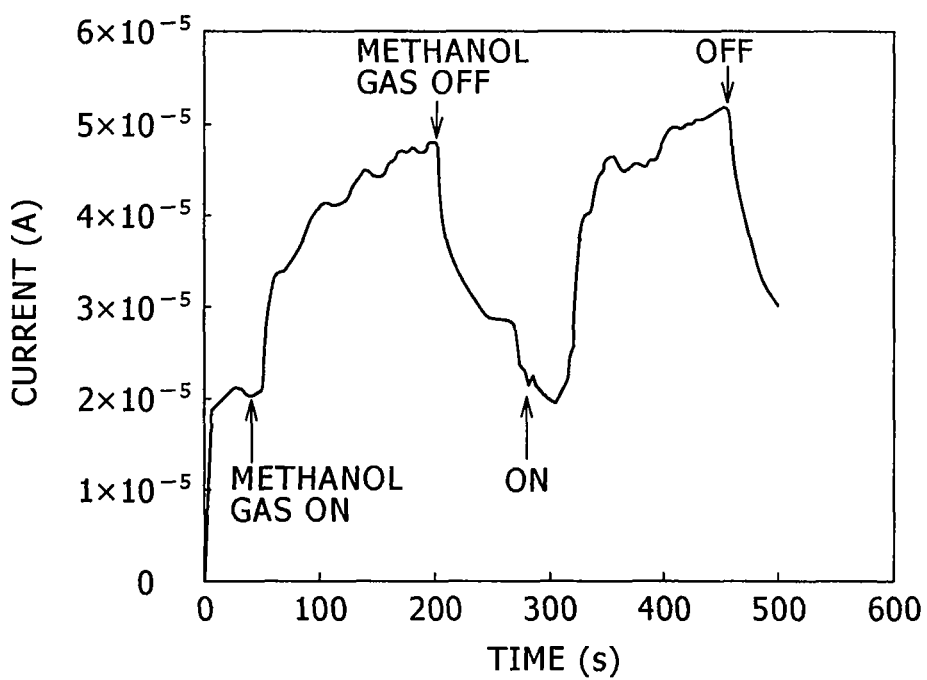
FIG. 17 is a graph showing how the gas sensor of metal oxide semiconductor (in one example of the present invention) changes in its output current as it detects methanol gas introduced intermittently into the atmosphere.

FIG. 17 is a graph showing how the gas sensor in this Example changes in its output current as it deterts methanol gas introduced intermittently into the atmosphere. In this experiment, change in current flowing through the gas sensor is measured as the flow of the methanol-containing gas to the gas sensor is turned on and off. It is noted from FIG. 19 that the current varies depending on the presence and absence of methanol at normal temperature.

Figure 18:
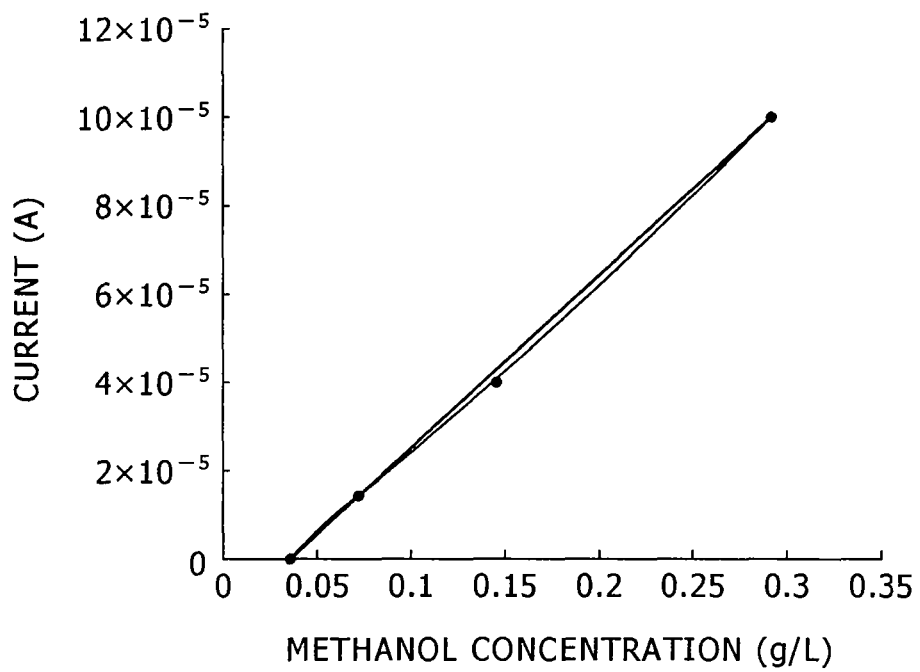
FIG. 18 is a graph showing how the gas sensor of metal oxide semiconductor (in one example of the present invention) changes in its output current at normal temperature depending on the concentration of methanol gas.

FIG. 18 is a graph showing how the gas sensor 30 of metal oxide semiconductor in this Example changes in its output current at normal temperature depending on the concentration of methanol gas. In this experiment, the methanol concentration is regulated by the amount of methanol introduced into the vessel. It is noted from FIG. 18 that current increases in proportion to the concentration of methanol in the vessel. The result indicates that the sensitivity corresponds to the amount of methanol evaporated.

Utility of the gas sensor in this Example as a sensor of expired gas is explained in the following. The gas sensor in this Example greatly varies in responsiveness according as the semiconductor material and the catalyst material are changed. A sample of the gas sensor as a sensor of expired gas was prepared from SnO$_2$ as the semiconductor material and gold as the catalyst material.

Figure 19:
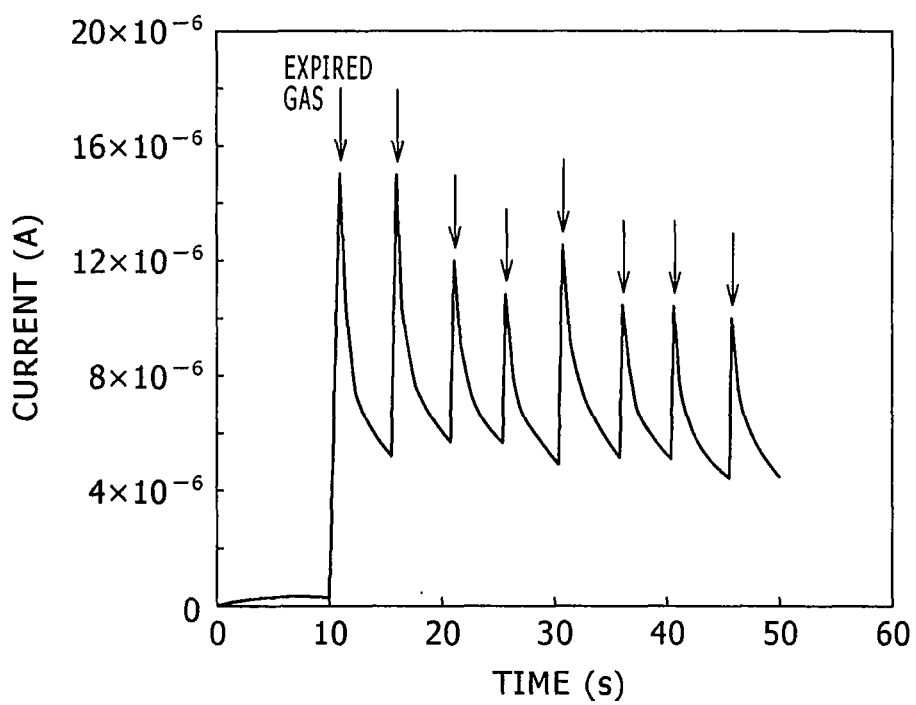
FIG. 19 is a graph showing how the gas sensor of metal oxide semiconductor (in one example of the present invention) changes in its output current as it detects expired gas.
Figure 20A:
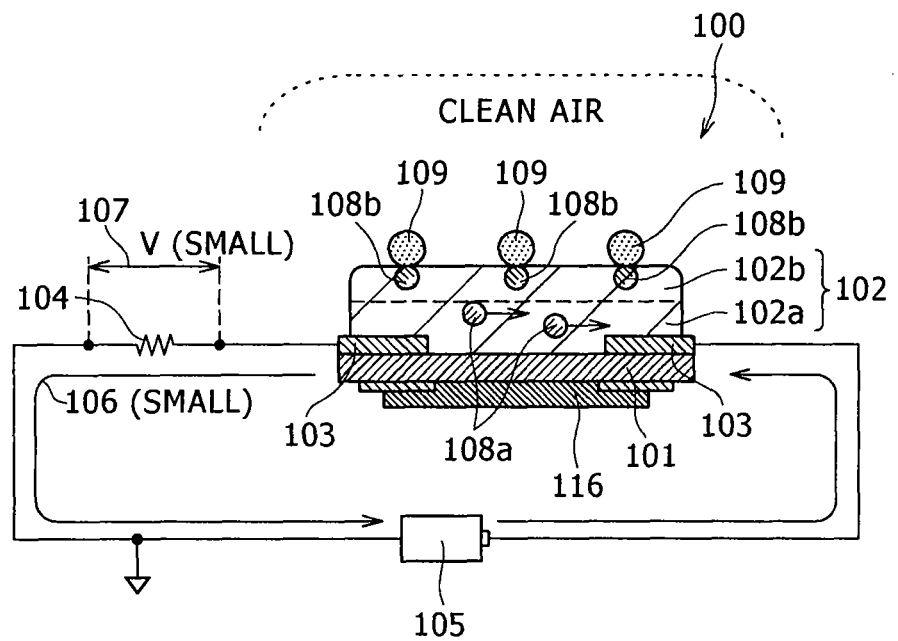
FIGS. 20A and 20B are diagrams each illustrating the principle on which a gas sensor with tin oxide works to detect a reducing gas.
Figure 20B:
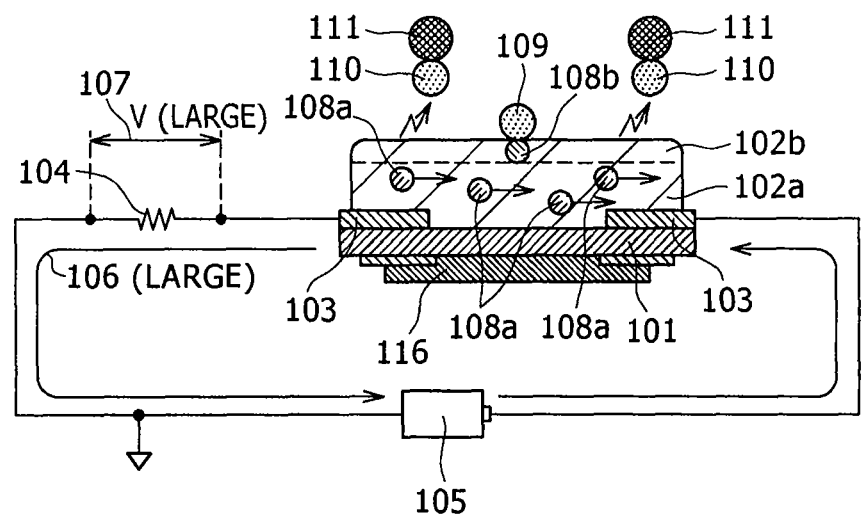

FIG. 19 is a graph showing how the sensor for expired gas changes in its output current as it detects human expired gas. It is noted that the sensor for expired gas rapidly responds to expired gas at intervals of five seconds. This gas sensor will be used as a sensor for the presence of a human.

The above-mentioned embodiments may be modified. For example, the gas-sensitive layer of mono-layer structure may be replaced by that of laminate structure which is formed by repeating several times the step of forming the mono-layer of metal oxide semiconductor microcrystals.

The gas sensor according to the embodiments is highly sensitive and stably operable at normal temperature and hence it permits power saving and size reduction. The method for production of the gas sensor according to the embodiments is highly productive and capable of uniform production at low cost. Thus, the gas sensor will find broader applications than conventional ones, such as the use as a methanol sensor for direct methanol fuel cells.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A gas sensor comprising:
   a gas-sensitive layer which changes in its characteristic properties upon contact with a detectable gas; and
   a sensitizer including a plurality of uniformly distributed discrete pieces in contact with the gas-sensitive layer;
   wherein said gas-sensitive layer has, as the main sensitive part, a polycrystalline layer composed of a plurality of uniform nano-size microcrystal particles which join together in a planar direction of the gas-sensitive layer,
   wherein the polycrystalline layer is a mono-layer which has only one microcrystal particle in a thickness direction of the gas-sensitive layer and a size of the sensitizer pieces is larger than the thickness of the polycrystalline layer,
   wherein the gas-sensitive layer is configured to sense the detectable gas at room temperature, and
   wherein the discrete pieces of the sensitizer are arranged in a lattice pattern with translational symmetry in the planar direction of the gas-sensitive layer.

2. The gas sensor of claim 1, wherein the microcrystal particles are approximately spherical polyhedra having a shape such that a ratio of a microcrystal particle diameter in the thickness direction of the gas-sensitive layer to a microcrystal particle diameter in the planar direction of the gas-sensitive layer ranges from about 0.8 to about 1.2.

3. The gas sensor of claim 2, wherein the ratio of the microcrystal particle diameter in the thickness direction of the gas-sensitive layer to the microcrystal particle diameter in the planar direction of the gas-sensitive layer ranges from 0.95 to 1.05.

4. The gas sensor of claim 2, wherein the gas-sensitive layer has a thickness no larger than 30 nm.

5. The gas sensor of claim 2, wherein the gas-sensitive layer has a thickness no smaller than 10 nm.

6. The gas sensor of claim 1, wherein the gas-sensitive layer has a surface with a honeycomb pattern having an area including borders of a repeating pattern of close-packed hexagonal units.

7. The gas sensor of claim 1, wherein the microcrystalline particles form a double Schottky barrier at their grain boundary.

8. The gas sensor of claim 1, wherein the gas-sensitive layer has a surface with a honeycomb pattern in the planar direction of the gas-sensitive layer and the discrete pieces of the sensitizer are positioned at the intersections of the honeycomb pattern, the honeycomb pattern having an area including borders of a repeating pattern of close-packed hexagonal units.

9. The gas sensor of claim 8, wherein the discrete pieces of sensitizer are also arranged in a honeycomb pattern.

10. The gas sensor of claim 1, wherein the sensitizer is a catalyst for the reaction that takes place on the surface of the gas-sensitive layer.

11. The gas sensor of claim 10, wherein the catalyst contains at least one species of elements selected from the group consisting of: platinum (Pt); palladium (Pd); silver (Ag); gold (Au); and ruthenium (Ru).

12. The gas sensor of claim 1, wherein the gas-sensitive layer is formed from a metal oxide semiconductor material that at least includes tin (IV) oxide ($SnO_2$).

13. The gas sensor of claim 1, wherein the gas-sensitive layer is formed from a metal oxide semiconductor material that is tin (IV) oxide ($SnO_2$).

14. The gas sensor of claim 1, wherein the gas-sensitive layer is formed from a metal oxide semiconductor material, wherein the metal oxide semiconductor material is at least one species selected from the group consisting of: tin (IV) oxide ($SnO_2$); zinc (II) oxide (ZnO); titanium (IV) oxide ($TiO_2$); indium (III) oxide ($In_2O_3$); vanadium (V) oxide ($V_2O_5$); tricobalt tetraoxide ($Co_3O_4$); and iron (III) oxide ($Fe_2O_3$).

\* \* \* \* \*